US 6,544,274 B2

(12) United States Patent
Danitz et al.

(10) Patent No.: US 6,544,274 B2
(45) Date of Patent: Apr. 8, 2003

(54) CLAMP HAVING BENDABLE SHAFT

(75) Inventors: David J. Danitz, Cupertino, CA (US); David E. Hegeman, San Francisco, CA (US); Terrence J. Buelna, Los Gatos, CA (US); Adam C. Gold, San Francisco, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 0 days.

(21) Appl. No.: 09/847,135

(22) Filed: May 2, 2001

(65) Prior Publication Data

US 2002/0165560 A1 Nov. 7, 2002

(51) Int. Cl.[7] ............................................. A61B 17/08
(52) U.S. Cl. ..................... 606/157; 606/158; 606/205
(58) Field of Search ........................ 606/151, 157, 606/158, 205; 600/123, 124, 125, 139, 141, 142, 40; 604/523, 524, 525, 535

(56) References Cited

U.S. PATENT DOCUMENTS

| 3,266,059 | A | * | 8/1966 | Stelle ........................ 138/120 |
| 4,054,128 | A | * | 10/1977 | Seufert et al. ............. 285/9.1 |
| 4,790,298 | A | * | 12/1988 | Trick ........................... 600/40 |
| 5,318,528 | A | | 6/1994 | Heaven ........................ 604/95 |
| 5,395,367 | A | | 3/1995 | Wilk ............................. 606/1 |
| 5,411,514 | A | | 5/1995 | Fucci et al. ................ 606/180 |
| 5,450,842 | A | | 9/1995 | Tovey ........................ 600/206 |
| 5,467,763 | A | | 11/1995 | McMahon et al. ......... 600/201 |
| 5,511,564 | A | | 4/1996 | Wilk ........................... 128/898 |
| 5,514,076 | A | | 5/1996 | Ley ............................ 600/206 |
| 5,514,115 | A | | 5/1996 | Frantzen .................... 604/281 |
| 5,520,222 | A | * | 5/1996 | Chikama ..................... 138/103 |
| 5,558,665 | A | | 9/1996 | Kieturakis .................... 606/1 |
| 5,593,416 | A | | 1/1997 | Donahue .................... 606/170 |
| 5,626,607 | A | | 5/1997 | Malecki et al. ............. 606/205 |
| 5,632,746 | A | | 5/1997 | Middleman ................. 606/78 |
| 5,680,982 | A | | 10/1997 | Schulze et al. ............ 600/139 |
| 5,752,969 | A | | 5/1998 | Cunci et al. ................ 606/167 |
| 5,772,578 | A | | 6/1998 | Heimberger et al. ....... 600/139 |
| 5,851,208 | A | | 12/1998 | Trott ........................... 606/80 |
| 5,876,330 | A | | 3/1999 | Grabover et al. .......... 600/129 |
| 5,916,147 | A | * | 6/1999 | Boury ....................... 600/139 |
| 6,019,722 | A | | 2/2000 | Spence et al. ............. 600/210 |
| 6,036,706 | A | | 3/2000 | Morejohn et al. ......... 600/158 |
| 6,139,563 | A | | 10/2000 | Cosgrove, III et al. .... 606/205 |
| 6,146,394 | A | | 11/2000 | Morejohn et al. ......... 606/158 |
| 6,156,047 | A | | 12/2000 | Spauling .................... 606/159 |
| 6,323,459 | B1 | * | 11/2001 | Maynard ..................... 219/209 |

FOREIGN PATENT DOCUMENTS

| JP | 404135554 | 11/1992 |
| WO | WO 95/00197 | 1/1995 |
| WO | WO 98/24371 | 6/1998 |
| WO | WO 98/40020 | 9/1998 |
| WO | WO 99/42036 | 8/1999 |

OTHER PUBLICATIONS

"Aorta Cross Clamp Assembly", Santilli, US patent application Publication No. US 2001/0049540 A1, publication date Dec. 6, 2001.

\* cited by examiner

*Primary Examiner*—Cary E. O'Connor
(74) *Attorney, Agent, or Firm*—Raymond Sun

(57) ABSTRACT

A clamp has a handle assembly, a gripping assembly having a pair of jaws that can be opened and closed to grip an element, and a shaft assembly. The shaft assembly has a flexible shaft having a proximal end that is coupled to the handle assembly and a distal end that is coupled to the gripping assembly. The flexible shaft also defines a bore that retains a cable which is operatively coupled to the handle assembly and to the gripping assembly. The shaft assembly also includes a retractable generally rigid covering which can be oriented in a first position where the covering exposes a portion of the flexible shaft, and in a second position where the covering completely covers the flexible shaft.

26 Claims, 18 Drawing Sheets

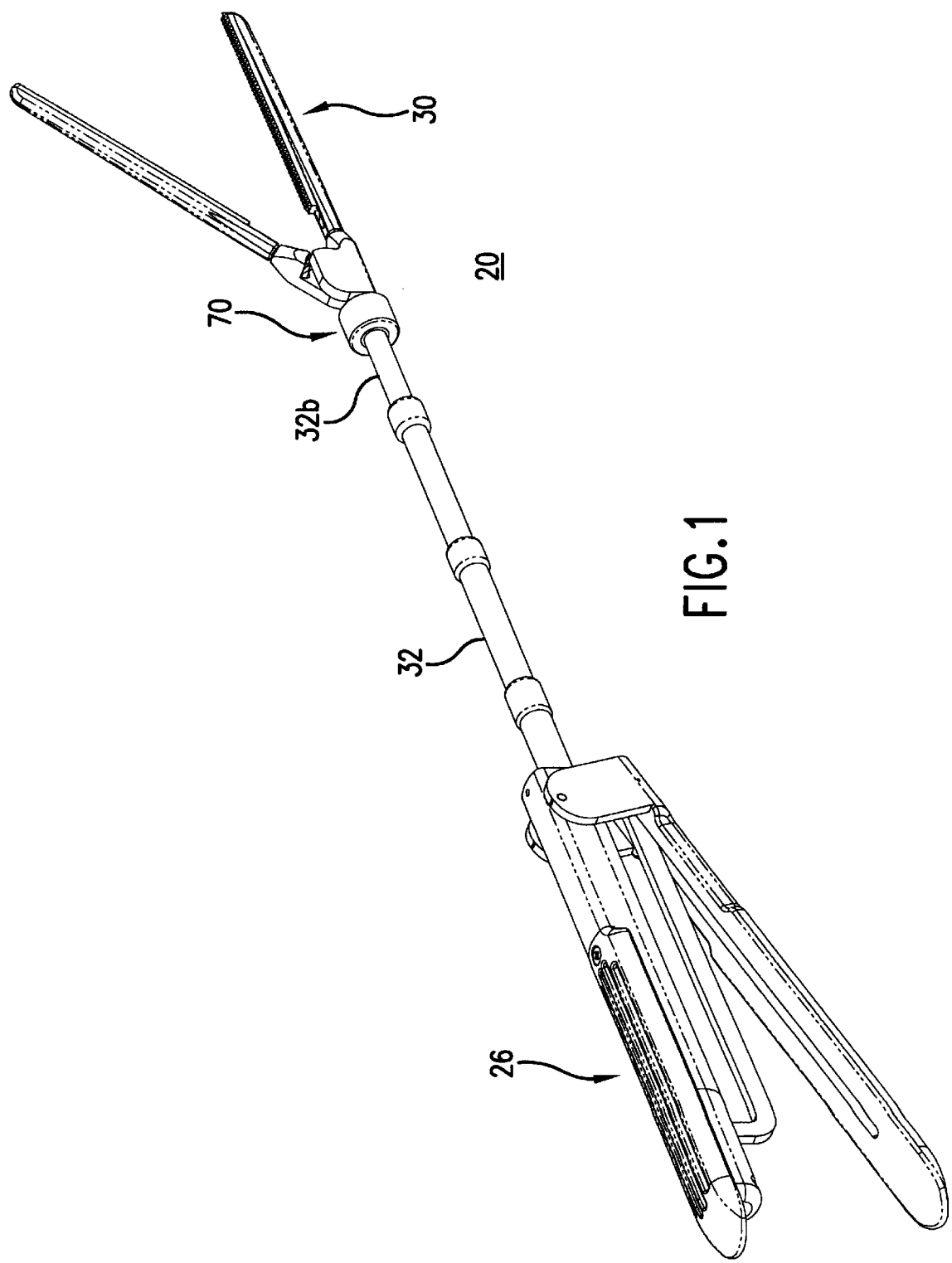

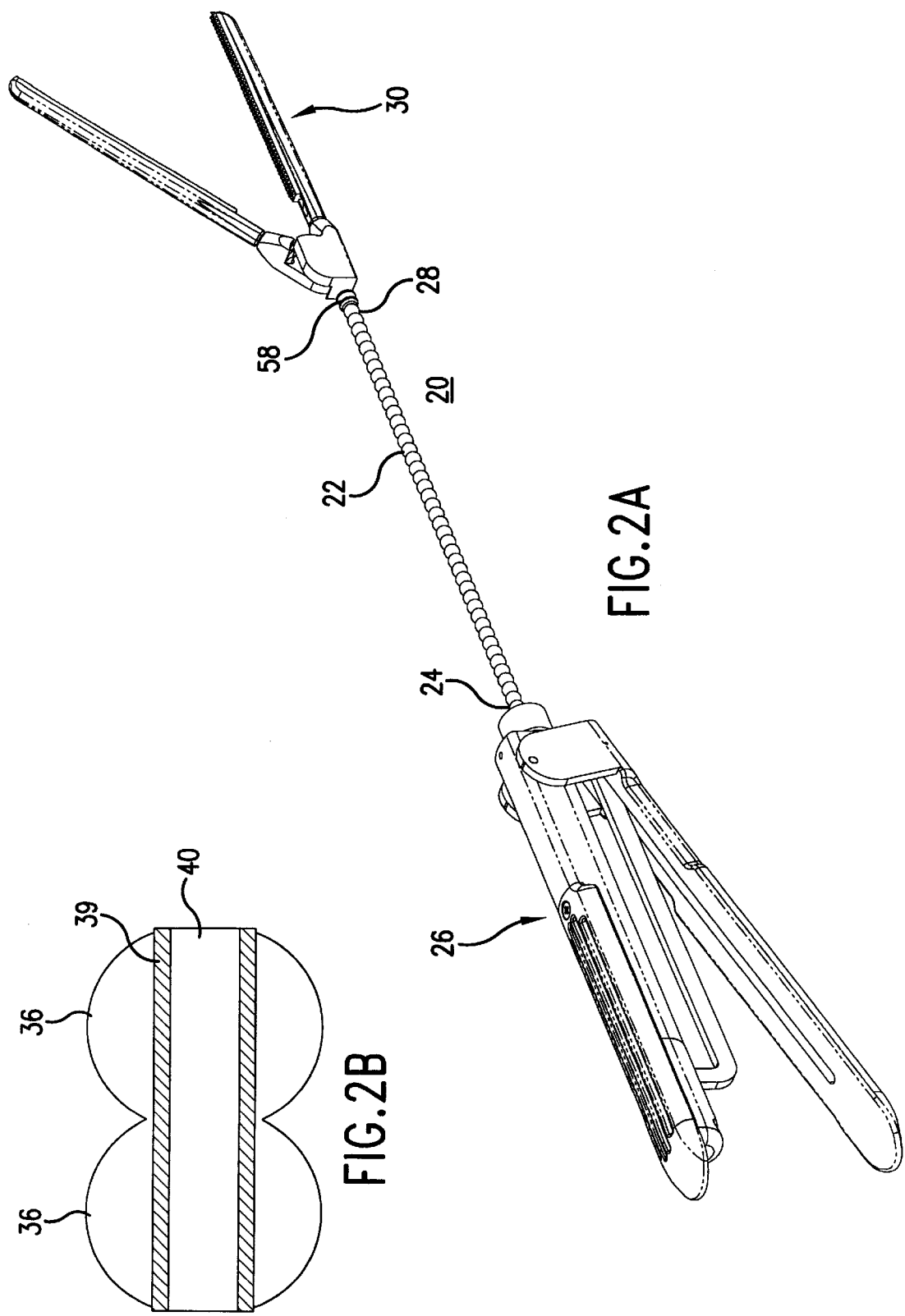

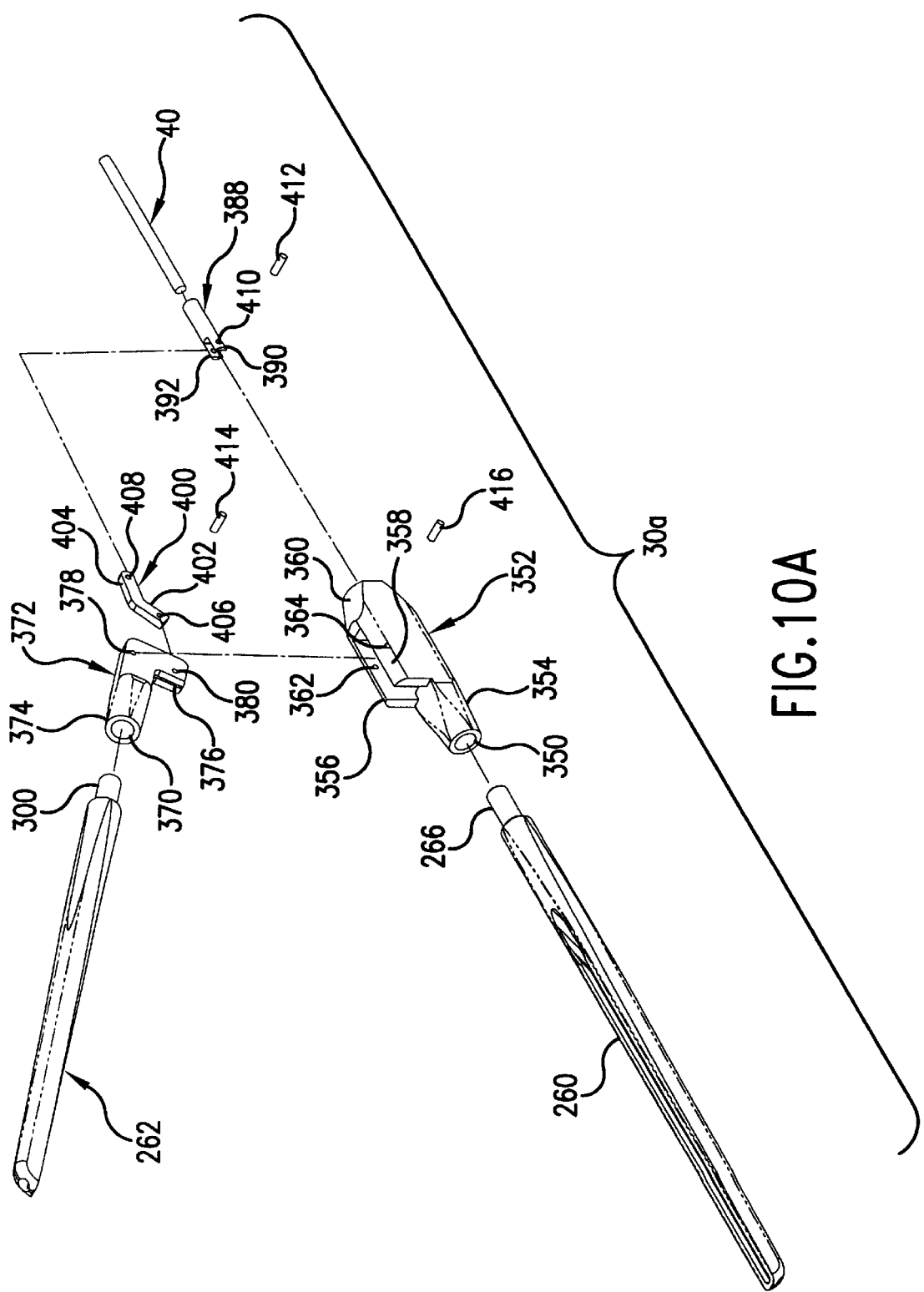

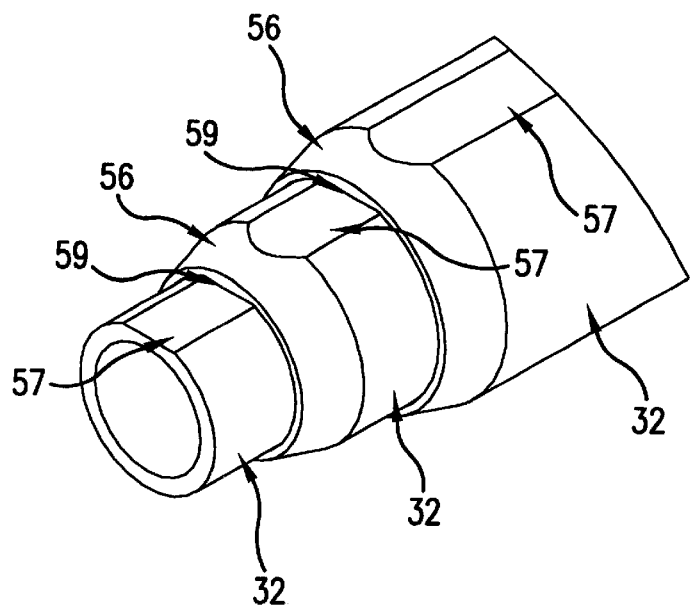
FIG.11
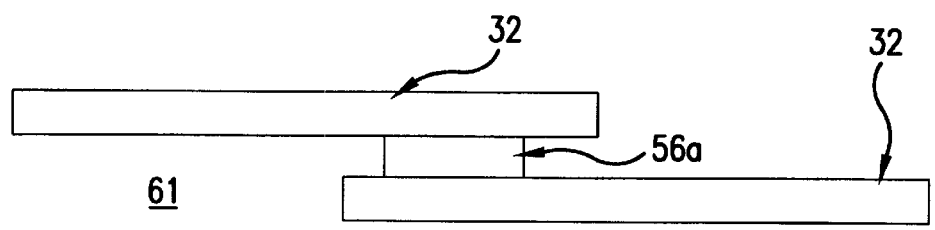
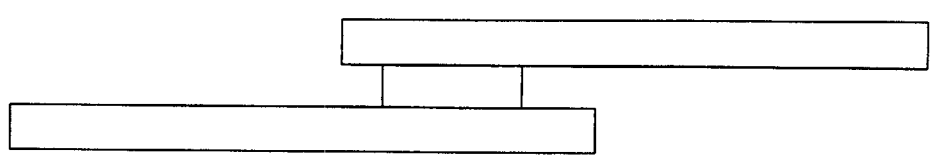
FIG.12

CLAMP HAVING BENDABLE SHAFT

BACKGROUND OF THE INVENTION

1. Field of the Invention

The present invention relates to medical devices, and in particular, to a clamping device that has a bendable shaft.

2. Description of the Prior Art

Clamping devices are typically used to occlude blood vessels during a surgical procedure. Conventional clamping devices are also known as clamps, and have a shaft that connects a pair of jaws with a handle at opposite ends thereof. The pair of jaws open and close about a pivot point in a motion that resembles that of a scissors. These conventional clamps are typically made from stainless steel and the shaft is therefore completely rigid. As a result, such conventional clamps are bulky and can interfere with the surgeon's access to the surgical site. To address this problem, elastic bands were sometimes used to hold the handles of the clamp away from the location of the surgical site.

With the increasing popularity of minimally invasive surgical procedures, access to the surgical site is reduced, thereby creating a need for smaller clamping devices, or clamping devices that can be moved away from the surgical site after the blood vessel has been clamped by the clamping device. As a result, the conventional clamps pose significant access problems to the surgeon when used during minimally invasive surgical procedures.

Thus, there remains a need for a clamping device that can be used to effectively clamp a blood vessel at a surgical site, while not interfering with the surgeon's access to the surgical site.

SUMMARY OF THE DISCLOSURE

It is an object of the present invention to provide a clamp that does not interfere with a surgeon's access to the surgical site during use.

It is another object of the present invention to provide a clamp that can effectively clamp a blood vessel at a surgical site.

It is yet another object of the present invention to provide a clamp whose handle can be moved away from the surgical site after the clamp has clamped the blood vessel.

It is yet another object of the present invention to provide a clamp that has a shaft which can be both completely rigid and completely flexible, with the rigid shaft being capable of withstanding axial loads, side loads, and moments applied to the jaws of the clamp.

It is yet another object of the present invention to provide a clamp that can be used in open and endoscopic surgeries.

The objectives of the present invention are accomplished by providing a clamp having a handle assembly, a gripping assembly having a pair of jaws that can be opened and closed to grip an element, and a shaft assembly. The shaft assembly has a flexible shaft having a proximal end that is coupled to the handle assembly and a distal end that is coupled to the gripping assembly. The flexible shaft also defines a bore that retains a cable which has a proximal end that is operatively coupled to the handle assembly and a distal end that is operatively coupled to the gripping assembly. A retractable and generally rigid covering is also provided and which can be oriented in a first position where the covering exposes a portion of the flexible shaft, and in a second position where the covering completely covers the flexible shaft.

The clamp can be utilized in a surgical procedure by first introducing the jaws through a surgical site or a trocar, then closing the jaws to grip a blood vessel, and then selectively withdrawing the covering from the flexible shaft so that a portion of, or the entire the region of, the flexible shaft is now completely flexible. At this time, the handle assembly can be moved away from the surgical site.

BRIEF DESCRIPTION OF THE DRAWINGS

FIG. 1 is a perspective view of a clamp according to the present invention with the shaft completely covered by telescoping tubes.

FIG. 2A is a perspective view of the clamp of FIG. 1 with the shaft not covered by telescoping tubes.

FIG. 2B is a cross-sectional view of a portion of the shaft of the clamp of FIG. 1.

FIG. 10A is an exploded perspective view of another embodiment of a gripping assembly that can be used with the clamp of FIG. 1.

FIG. 11 is an enlarged sectional view of a plurality of nested telescoping tubes according to one embodiment of the present invention.

FIG. 12 is a cross-sectional view illustrating the nesting of two adjacent telescoping tubes according to another embodiment of the present invention.

DETAILED DESCRIPTION OF THE PREFERRED EMBODIMENTS

Figure 3A:
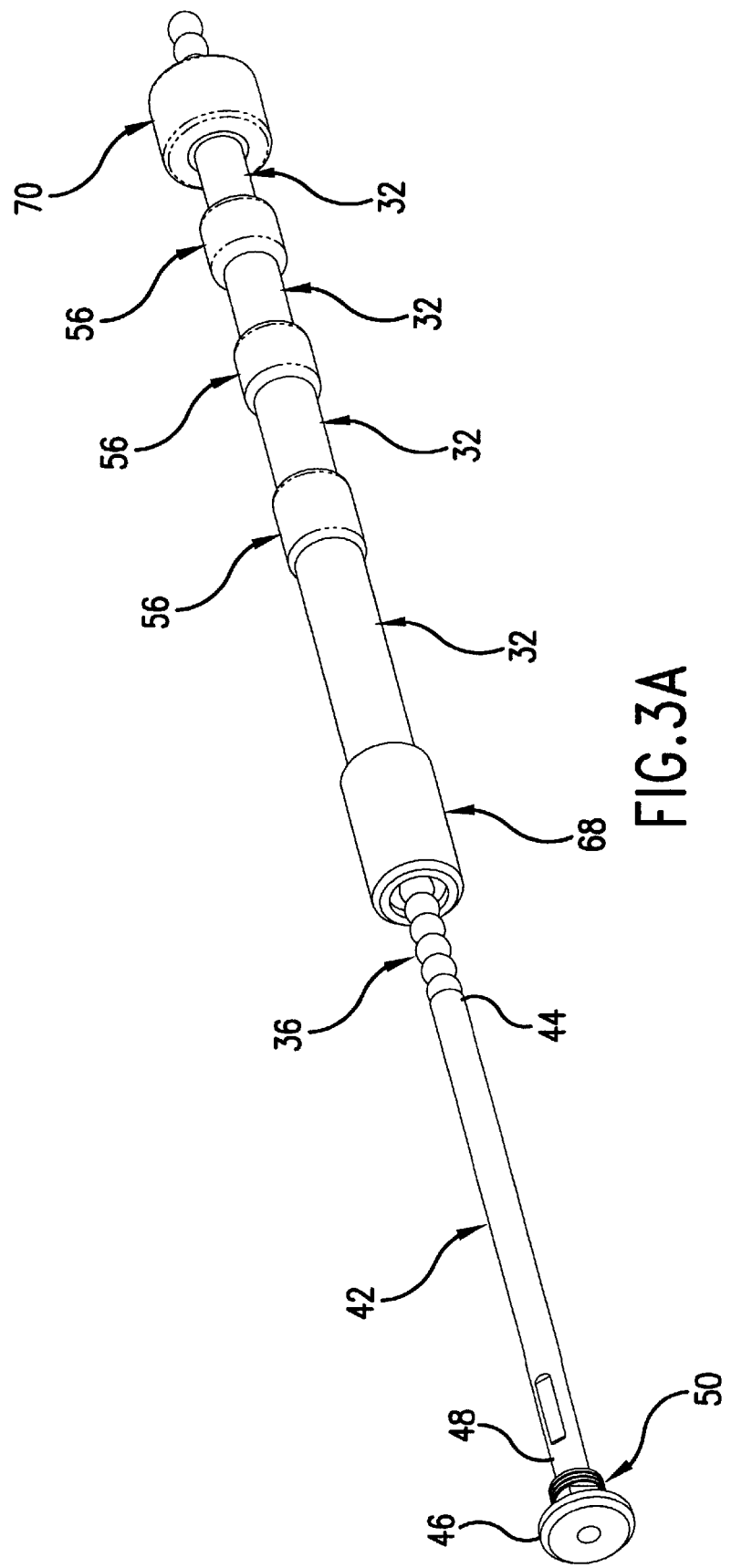
FIG. 3A is a perspective sectional view of the shaft assembly of the clamp of FIG. 1.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

The present invention provides a clamping device that has a flexible and bendable shaft that can be selectively supported by a plurality of generally rigid telescoping tubes. When the clamping device is being held and controlled by the surgeon prior to clamping a blood vessel, the telescoping tubes can be deployed to completely cover and support the flexible shaft so that the entire clamping device is generally rigid. After the clamping device has been used to clamp a blood vessel, the telescoping tubes can be withdrawn so that the flexible shaft can be conveniently bent by the surgeon to a position or location so that the handle assembly does not interfere with access to the surgical site.

FIGS. 1 and 2 are perspective views illustrating the clamp 20 of the present invention. The clamp 20 has a shaft assembly having a flexible shaft 22 having a proximal end 24 that is operatively connected to a handle assembly 26, and a distal end 28 that is operatively connected to a gripping assembly 30. A plurality of telescoping tubes 32 can be withdrawn and stored in nested fashion inside the handle assembly 26 (see FIG. 2), or can be fully deployed to completely cover the shaft 22 (see FIG. 1).

Shaft Assembly and Telescoping Tubes

Figure 5:
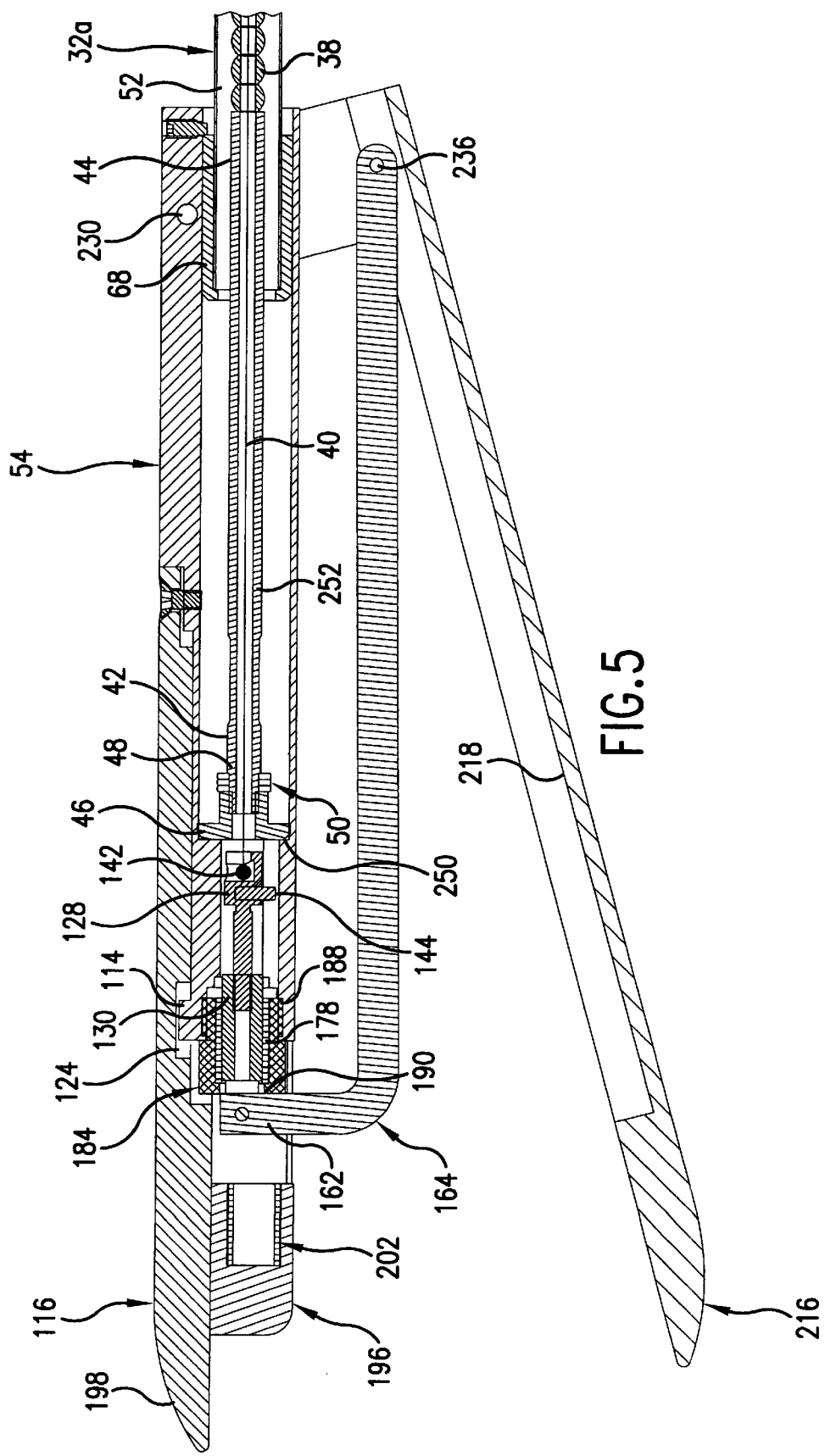
FIG. 5 is a cross-sectional view of the handle assembly of the clamp of FIG. 1 with the telescoping tubes deployed over the shaft.

Referring now to FIGS. 2A, 2B and 3A, in one embodiment, the shaft 22 can be made up of a plurality of beads 36. In one non-limiting preferred embodiment, the shaft 22 can be flexible to the point where it would be completely flexible (in other words, limp, flaccid, pliable, compliant and not stiff) when the shaft 22 is not supported by any other element, yet despite being completely flexible, is still capable of withstanding axial loads. The beads 36 are preferably made of a material that is hard and stiff, with good wear properties. Non-limiting examples of such a material for the beads 36 include stainless steel and plastic. Each bead 36 can have, in one embodiment, an outside diameter of about 5/32 inches. Preferably, between 20 to 200 beads 36 can be connected together to form the shaft 22. As shown in FIGS. 2B and 5, each bead 36 can be provided with a through-hole or bore 38 that is slid over a teflon tubing 39 so as to form a longitudinal bore through the shaft 22, with an internal wire cable 40 retained inside the teflon tubing 39. The beads 36 are lined up side-by-side in abutting fashion along the teflon tubing 39 to form the shaft 22. The cable 40 is always in tension, and is utilized to control the opening and closing of the jaws of the gripping assembly 30, as will be described in greater detail below. The cable 40 can be embodied in the form of any conventional cable that is used in clamping devices, and can be made, for example, from stainless steel or tungsten, among other examples.

Figure 6:
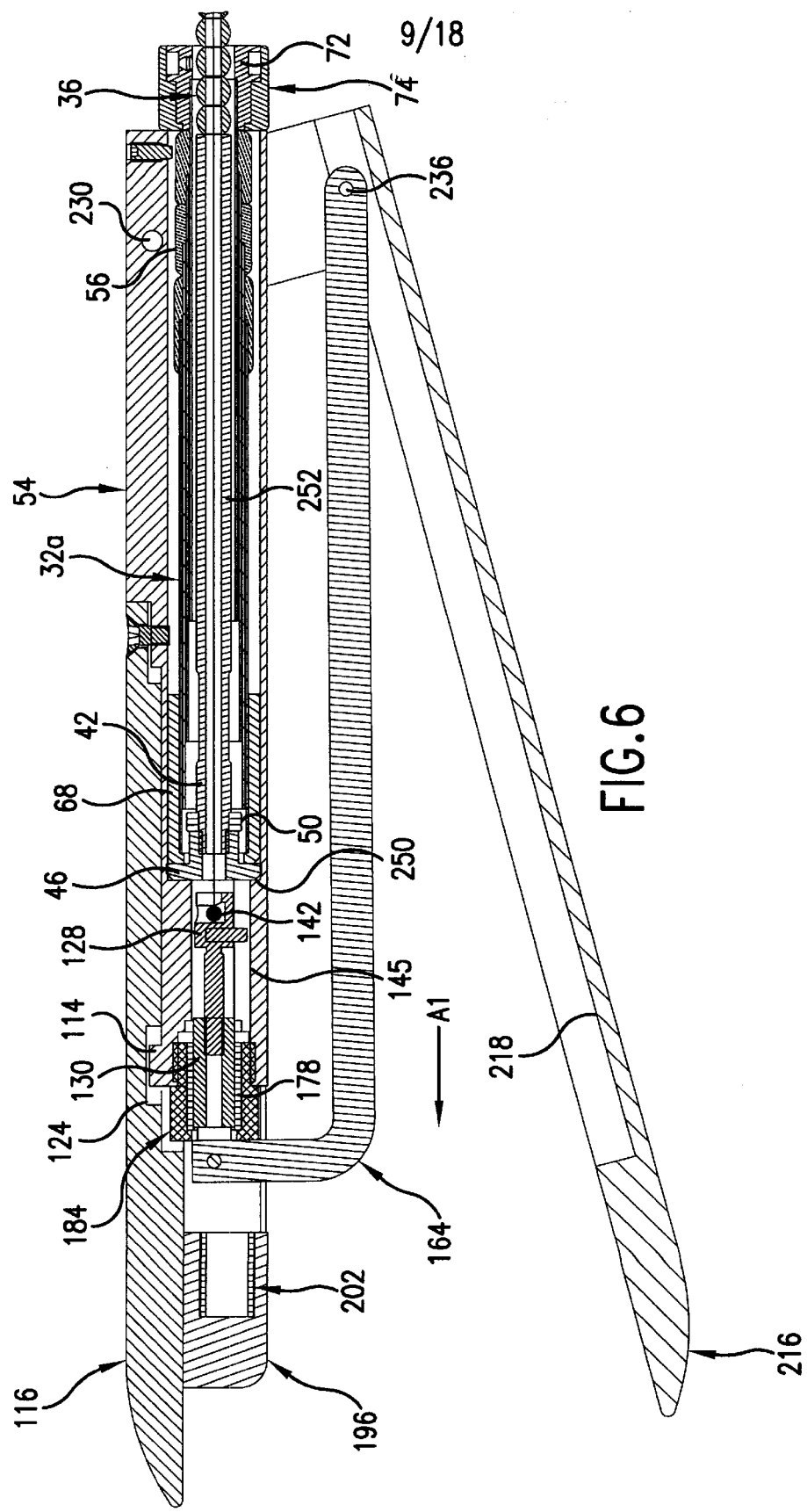
FIG. 6 is a cross-sectional view of the handle assembly of the clamp of FIG. 1 with the telescoping tubes retained inside the handle assembly.

The proximal end 24 of the shaft 22 abuts a distal end 44 of a proximal tube 42 that is secured inside the handle assembly 26, as shown in FIGS. 5 and 6. The teflon tubing 39 and the cable 40 extend through the interior of the proximal tube 42. A stop member 46 is threadably connected to the proximal end 48 of the tube 42. A plurality of washers 50 are threadably engaged along the external threads at the proximal end 48 of the tube 42. The tube 42 is threaded into the stop member 46 until the washers 50 are in compression. Enough torque can be applied to prevent the threaded connection from coming loose.

The washers 50 allow the length of the threaded connection between the tube 42 and the stop member 46 to be adjusted by the manufacturer of the clamp 20 during the assembly of the handle assembly. Adjusting the length of the threaded connection between the tube 42 and the stop member 46 allows the length of the shaft 22 to be adjusted, which in turn allows for (i) tensioning of the cable 40, and (ii) adjustment the maximum opening angle of the jaws 260, 262 of the gripping assembly 30. In this regard, the washers 50 facilitate the adjustment of the threaded connection between the tube 42 and the stop member 46 by varying the number of washers 50. The effect of the number of washers 50 on adjusting the threaded connection can be illustrated as follows. For example, by adding (or providing) additional washers 50, the length of the threaded connection (between the stop member 46 and the tube 42) is decreased. In this situation, the stop member 46 and the tube 42 are moved away from each other, thereby increasing the length of the shaft 22. By increasing the length of the shaft 22, the length of the cable 40 that protrudes from each end of the shaft 22 is decreased. This effectively decreases the length of the cable 40 relative to the shaft 22, which increases the maximum tension in the cable 40 and decreases the maximum opening angle of the jaws of the gripping assembly 30. Similarly, by decreasing the number of washers 50, the length of the threaded connection is increased. In this situation, the stop member 46 and the tube 42 are moved towards each other, thereby decreasing the length of the shaft 22. This effectively increases the length of the cable 40 relative to the shaft 22, which decreases the maximum tension in the cable 40 and increases the maximum opening angle of the jaws of the gripping assembly 30.

Instead of the washers 50, it is also possible to use a single lock nut (not shown). The manufacturer can increase or decrease the length of the threaded connection between the tube 42 and the stop member 46, and then tighten the lock nut to prevent the threaded connection from coming loose.

A plurality of telescoping tubes 32 can be used to provide rigidity to the beaded shaft 22. Each telescoping tube 32 has an inner bore 52. Any number of telescoping tubes 32 can be provided, and according to one embodiment of the present invention, two to five telescoping tubes 32 are provided. Each telescoping tube 32 can have any desired cross-section (e.g., circular, square, rectangular or elliptical, among others), and is preferably made from a substantially rigid material, such as plastic, aluminium, titanium and stainless steel, among others. The proximal-most telescoping tube 32a has the largest diameter and largest inner bore 52, while the diameters and sizes of the inner bores of the intermediate telescoping tubes 32 become progressively smaller until the distal-most telescoping tube 32b, which has the smallest diameter and smallest inner bore 52. This configuration allows the plurality of telescoping tubes 32 to be nested within each other and stored inside the tube housing 54 of the handle assembly 26. Each telescoping tube 32 also has a bushing 56 that is provided on the outer surface at the distal end of each telescoping tube 32, with the bushings 56 functioning as stop members (see FIG. 6) when the plurality of telescoping tubes 32 are withdrawn and retained inside the tube housing 54. A proximal tube bushing 68 is attached to the proximal-most telescoping tube 32a, and its outside diameter is adapted to slide inside the bore 110 of the tube housing 54 (see FIGS. 4A, 5 and 6) that is described in greater detail hereinbelow.

In addition to functioning as stop members, the bushings 56 also function to promote smooth sliding of the telescoping tubes 32 within each other, and to promote stiffness to the region of the shaft 22 when the shaft 22 is completely covered by the telescoping tubes 32. With respect to the promotion of the smooth sliding of the telescoping tubes 32 within each other, the bushings 56 can be made of a harder stainless steel than the telescoping tubes 32, or can be made from plastic. The smooth sliding of the telescoping tubes 32 will be achieved by the smooth surface finish of the bushings 56 and the telescoping tubes 32. If the bushings 56 are made of plastic, the smooth sliding will also be achieved by the low coefficient of friction between the telescoping tubes 32 and the bushings 56. With respect to the promotion of stiffness, the overlap between the ends of adjacent telescoping tubes 32 functions to counter any side-load or moment applied to the jaws of the gripping assembly 30.

If the cross-section of the telescoping tubes 32 is round, then a flat surface (e.g., see 57 in FIG. 11) can be machined or otherwise provided on the outer surface of each telescoping tube 32, and another flat surface 59 may be machined in the inner surface of the bore of each bushing 56. This will prevent the telescoping tubes 32 from rotating with respect to each other when the shaft 22 is torqued during use of the clamp 20.

In addition, the bushings 56 need not be provided on the outer surface of each telescoping tube 32. As shown in FIG. 12, the bushings 56a can be provided in the bore 61 of each telescoping tube 32, and adapted to slide against the outer surface of the adjacent telescoping tube 32.

Figure 3B:
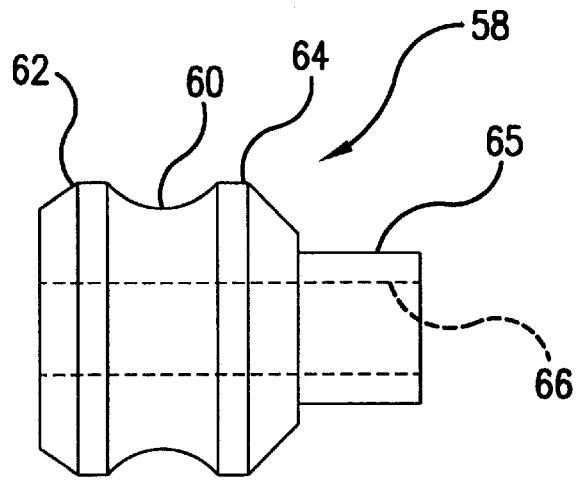
FIG. 3B is a side plan view of a locking hub on the shaft assembly of FIG. 3A.

As shown in FIGS. 2A, 7A, 8 and 9, a locking hub 58 is provided at the distal end 28 of the shaft 22. FIG. 3B provides an isolated view of the locking hub 58, which has an annular concave channel 60 between two annular ends 62 and 64. The hub 58 also has a shaft 65 having a bore 66 through which the cable 40 extends.

Figure 3C:
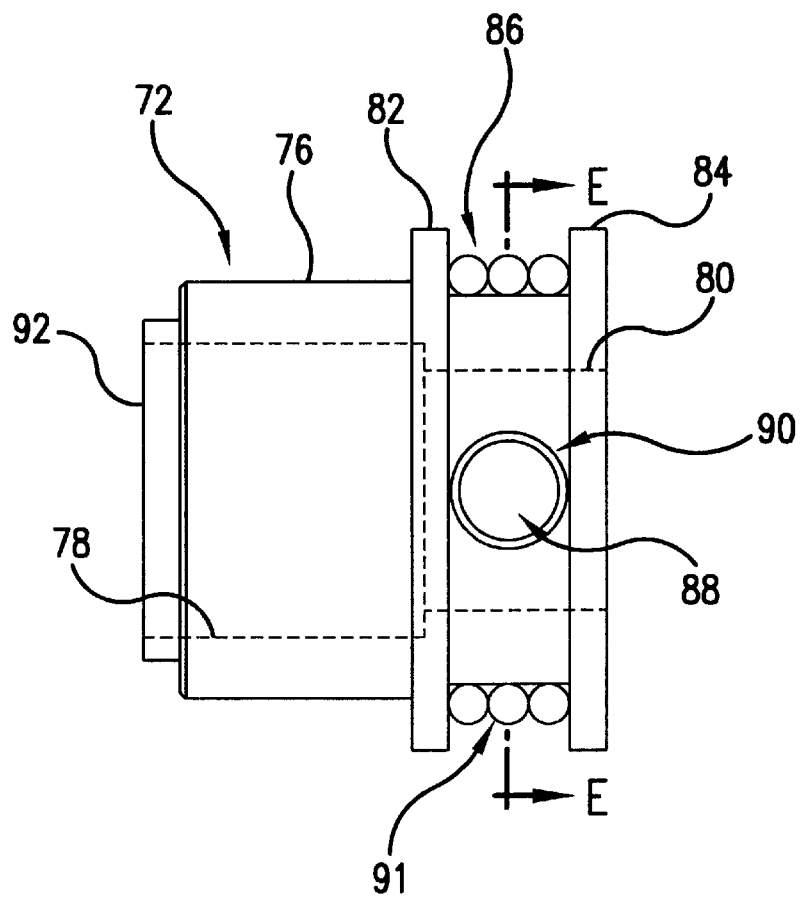
FIG. 3C is a side plan view of an inner lock housing.
Figure 9:
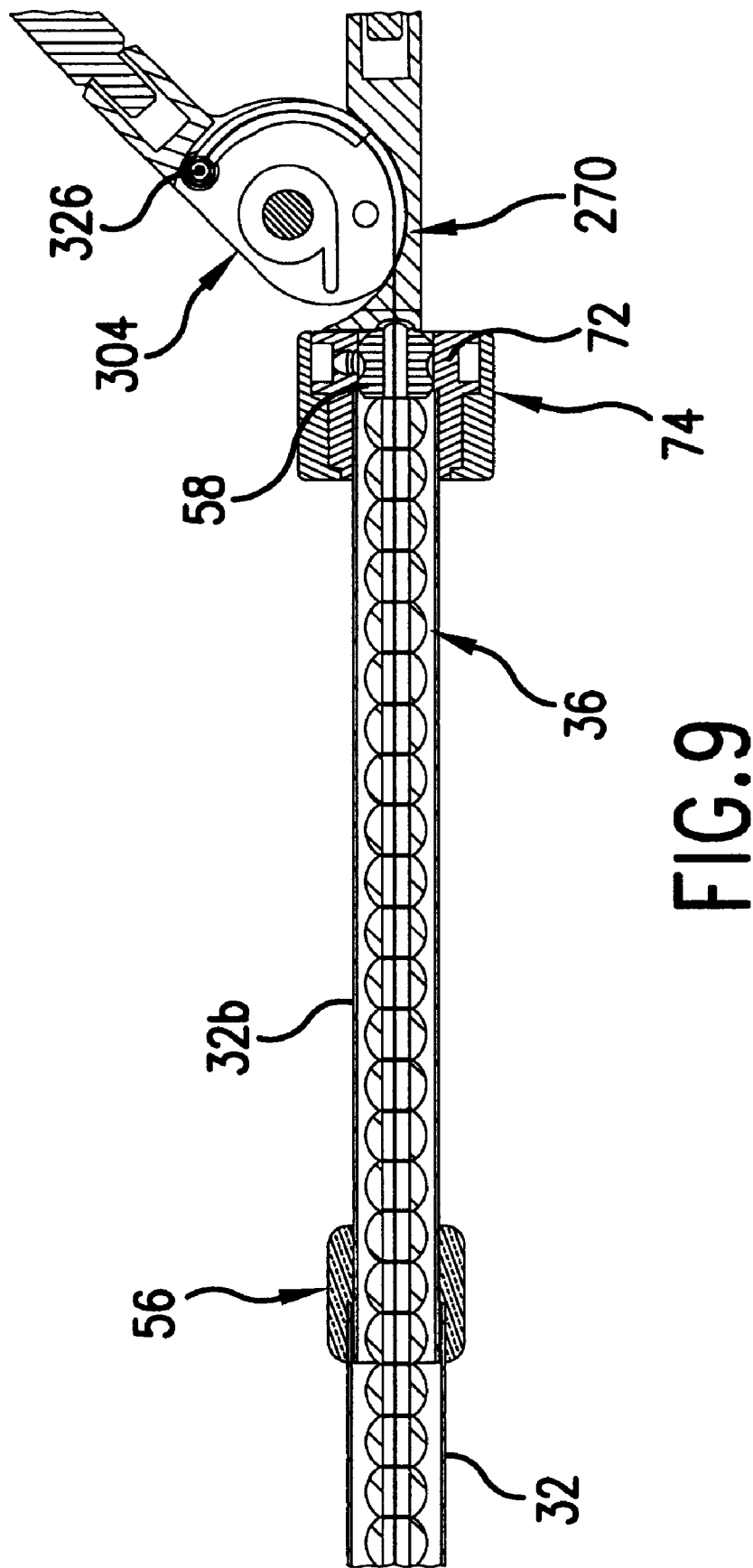
FIG. 9 is a cross-sectional view of the gripping assembly of FIG. 7A with the telescoping tubes deployed over the shaft.

As shown in FIGS. 1, 6 and 9, a locking mechanism 70 is attached to the distal-most end of the distal-most telescoping tube 32b. The locking mechanism 70 is adapted to engage the locking hub 58 in the manner described below to ensure that the entire shaft 22 is covered and supported by the telescoping tubes 32, and to prevent rotation of the jaws of the gripping assembly 30 when the locking mechanism 70 is engaged with the locking hub 58. The locking mechanism 70 includes an inner lock housing 72 and an outer lock housing 74. FIGS. 3C and 3E provide isolated views of the inner lock housing 72, which has a generally cylindrical body 76 with a bore extending therethrough. The bore has a proximal section 78 that communicates directly with a distal section 80. The proximal section 78 has a greater diameter than the distal section 80, and is adapted to attach and retain the distal-most end of the distal-most telescoping tube 32b, as shown in FIG. 6. Two annular ridges 82 and 84 extend from the cylindrical body 76 at the location of the distal section 80 of the bore, and define an annular space 86 therebetween. A plurality of radial holes 90 are positioned in spaced-apart manner about the cylinder body 76 in the annular space 86. For example, four holes 90 can be provided and spaced apart equally by 90 degrees with respect to each other. A ball 88 is seated within each hole 90, and protrudes slightly into the bore of the distal section 80. A chamfered step 89 is provided in each hole 90 to prevent the ball 88 from falling into the bore of the distal section 80. A coil spring 91 is wrapped around the cylinder body 76 at the annular space 86 to keep the balls 88 in contact with the chamfered steps 89. The parts of the ball 88 that protrude into the bore of the distal section 80 facilitate removable engagement with the concave channel 60 of the locking hub 58 in the following manner: when the locking hub 58 is inserted into the bore of the distal section 80, the annular end 62 of the locking hub 58 forces the balls 88 radially outwardly. When the balls 88 are axially aligned with the concave channel 60, the coil spring 91 forces the protruding parts of the balls 88 into the concave channel 60. This combination of an outward radial force (from the annular end 62) and an inward radial force (from the coil spring 91) locks the inner lock housing 72 with the locking hub 58. A narrowed annular end 92 is provided adjacent the proximal end of the cylindrical body 76.

Figure 3D:
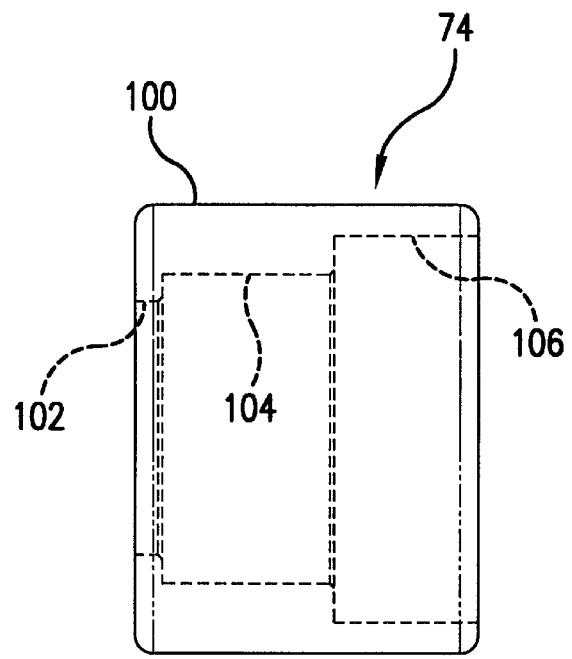
FIG. 3D is a side plan view of an outer lock housing.
Figure 3E:
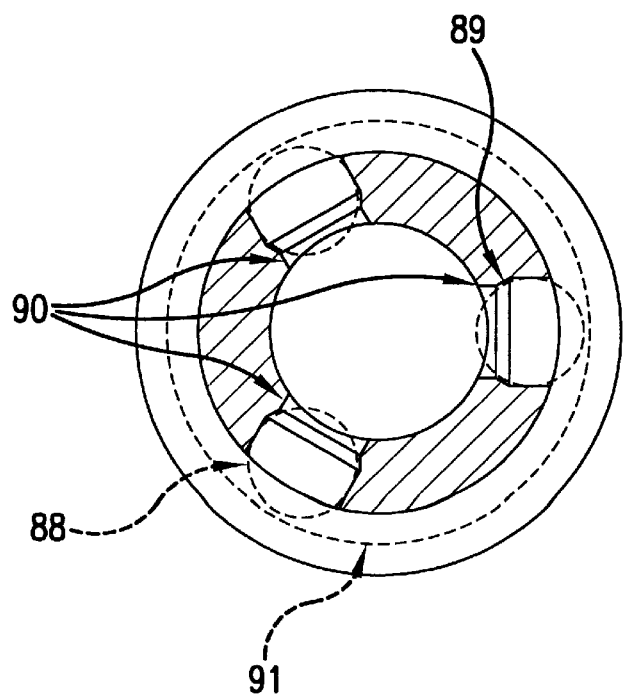
FIG. 3E is a cross-sectional view taken along line E—E of FIG. 3C.

FIG. 3D provides an isolated view of the outer lock housing 74, which has a generally cylindrical body 100 with a bore that has three different sections, a first section 102 having the narrowest diameter and adapted to receive the end 92 of the inner lock housing 72, a second section 104 having a diameter larger than that of the first section 102 and adapted to receive the region of the inner lock housing 72 at about the location of the proximal section 76, and a third section 106 having a diameter larger than that of the second section 104 and adapted to receive the wider-diameter ridges 82 and 84.

In use, the outer lock housing 74 is secured (e.g., by welding, glue, or biasing) over the inner lock housing 72. The outer lock housing 74 protects the balls 88 and the coil spring 91, while retaining the coil spring 91 inside the annular space 86 and the balls 88 in the holes 90.

Although the present invention illustrates the flexible shaft 22 as being comprised of a string of connected beads 36, it is possible to provide the shaft 22 in the form of any material that is flexible. Examples include superelastic metal tubes, closed wound springs, goosenecks, and thin wall tubes, among others. It is also possible for the beads 36 to be provided in different shapes, such as cylindrical beads, oval beads, square beads, and beads with mating ball and socket joints. Whatever material is used, the bead 36 or the material that makes up the flexible shaft 22 must be able to withstand compressive loads (as a reaction to the tension in the cable 40) while remaining flexible.

The Handle Assembly

The handle assembly 26 is best illustrated in FIGS. 4–6. The handle assembly 26 has a tube housing 54 which is essentially a cylindrical tube having a bore 110 extending therethrough. The tube housing 54 has a planar recessed region 112 on one side thereof that is positioned between a proximal annular flange 114 and the approximate center of the tube housing 54. The recessed region 112 is adapted to receive a stationary handle piece 116 whose distal end can be connected to the recessed region 112; for example, by threading a screw 118 through an opening 120 in the distal end of the handle piece 116 and a threaded hole 122 at the distal end of the recessed region 112. The handle piece 116 also has a groove 124 provided in its inner surface that is adapted to receive the flange 114 (see FIG. 5).

The handle assembly 26 houses a cable terminator assembly that comprises a cable holder 128 and an adjuster piece 130. FIG. 4B provides an isolated view of the cable holder 128, which has a proximal shaft 132 and a generally cylindrical cable head 134 attached to the shaft 132. The front face 136 of the cable head 134 has a key-shaped slot cut from the outer surface through the center of the cable head 134. The key-shaped slot has a rounded section 138 inside the cable head 134, and a longitudinal section 140 at the front face 136 that is smaller in size than the rounded configuration. The bulbous end 142 of the cable 40 (see FIG. 5) is retained inside the rounded section 138, and the cable 40 extends through the longitudinal section 140. The bulbous end 142 is securely retained inside the rounded section 138 because the bulbous end 142 is larger than the longitudinal section 140 in size. A dowel pin 144 is provided on the cable head 134 and is adapted to ride along a keyway 145 (see FIGS. 5 and 6) inside the tube housing 54 to prevent the cable holder 128 from rotating when the adjuster piece 130 is turned to adjust or calibrate the tension of the cable 40 and the maximum opening angle of the jaws of the gripping assembly 30.

Figure 4A:
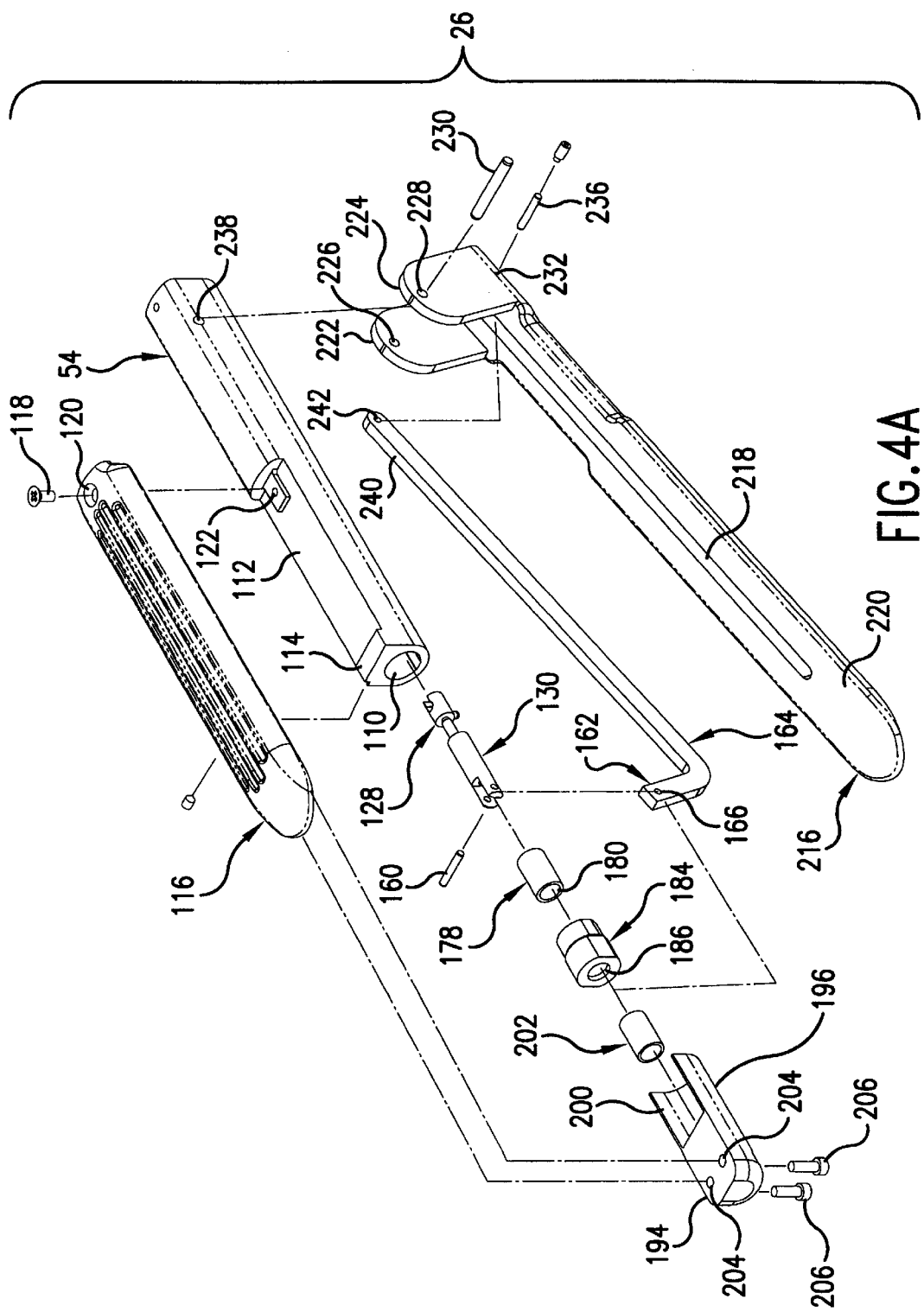
FIG. 4A is an exploded perspective view of the handle assembly of the clamp of FIG. 1.
Figure 4B:
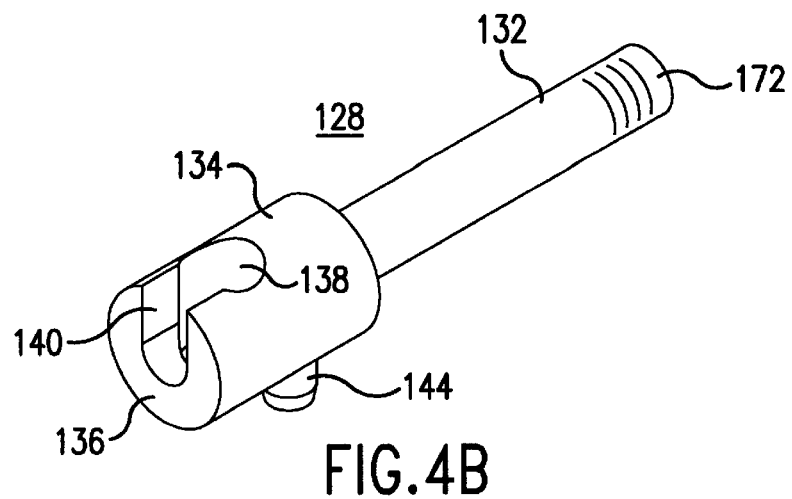
FIG. 4B is a perspective view of a cable housing of the handle assembly of FIG. 4A.
Figure 4C:
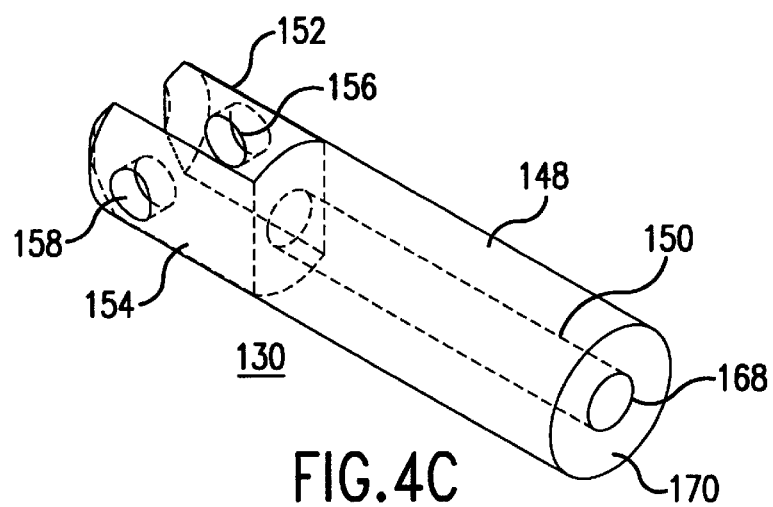
FIG. 4C is a rear perspective view of an adjuster piece of the handle assembly of FIG. 4A.

FIG. 4C provides an isolated view of the adjuster piece 130, which has a generally cylindrical body 148 having a threaded bore 150 extending therethrough. Two opposing walls 152 and 154 extend from the proximal end of the cylindrical body 148 to define an internal space therebetween. Each wall 152 and 154 has an opening 156 and 158, respectively, that are aligned with each other and through which a pin 160 can be extended (see FIG. 4A). The internal space between the walls 152, 154 is adapted to receive a hooked end 162 of a transmission link 164, with the pin 160 inserted through the openings 156, 158, and an aligned opening 166 in the hooked end 162 to create a pivoting connection between the hooked end 162 and the adjuster piece 130. The shaft 132 of the cable holder 128 is inserted into the bore 150 via an opening 168 in the distal face 170 of the adjuster piece 130. The shaft 132 can be provided with external threads 172 for threadably engaging the internal threads in the bore 150.

In addition to adjusting or calibrating the maximum tension in the cable 40 and the maximum opening angle of the jaws of the gripping assembly 30 by adjusting the length of the shaft 22, the maximum tension in the cable 40 and the maximum opening angle of the jaws of the gripping assembly 30 can also be adjusted or calibrated by changing the length of the cable 40 directly. The maximum tension of the cable 40 and the maximum opening angle of the jaws of the gripping assembly 30 can be adjusted or calibrated by turning the adjuster piece 130 when the pin 160 does not couple the adjuster piece 130 to the hooked end 162. For example, when the pin 160 is removed from the openings 156, 158 and 166, the hooked end 162 of the transmission link 164 can be separated from the adjuster piece 130. This can only be done by the manufacturer. By rotating the adjuster piece 130, the threads 172 on the cable holder 128 translate in the threaded bore 150 to either increase or decrease the length of the cable 40 (depending on the direction of rotation). By decreasing the length of the cable 40, the jaws of the gripping assembly 30 close slightly, and the maximum force that the cable 40 can transmit to the jaws is increased. By increasing the length of the cable 40, the jaws open slightly, and the maximum force that the cable 40 can transmit to the jaws is decreased. When the adjuster piece 130 is being rotated, the cable holder 128 cannot rotate because the dowel pin 144 is retained in the keyway 145 of the tube housing 154.

The handle assembly 26 further houses a plastic bushing 178 that is cylindrical in configuration and has a hollow bore 180 through which the adjuster piece 130 can slide in a reciprocal manner. A bushing housing 184 has a bore 186 that houses the bushing 178. Referring also to FIG. 5, the bushing housing 184 has external threads 188 (see FIG. 4A) for engaging the internal threads provided in the bore 110 of the tube housing 54 adjacent the proximal end thereof (i.e., at the region of the flange 114). The proximal end of the bushing housing 184 has a shoulder 190 that acts as a proximal stop to retain the bushing 178 inside the bore 186.

Figure 4D:
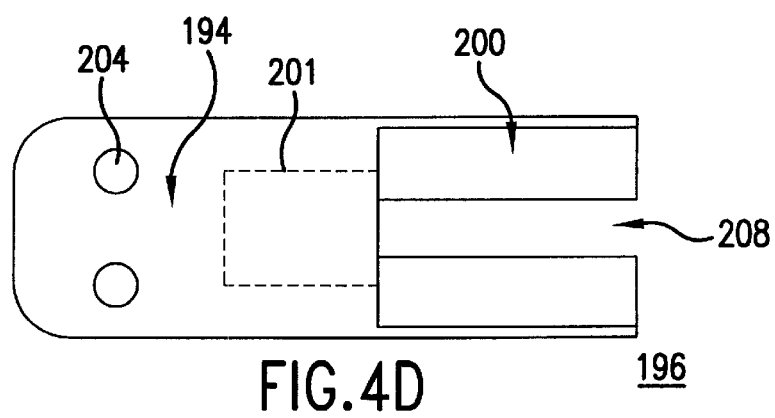
FIG. 4D is a top plan view of a spring housing of the handle assembly of FIG. 4A.

As shown in FIGS. 4A and 5, a spring housing 196 is attached to the proximal end 198 of the handle piece 116. FIG. 4D provides an isolated view of the spring housing 196, which has a solid section 194 and a groove section 200. A bore 201 is provided in the solid section 194, and a compression spring 202 is retained in the bore 201. The compression spring 202 is normally biased against the hooked end 162 of the transmission link 164 (which travels inside the groove section 200) in order to keep the handle pieces 116, 216 of the handle assembly 26 open when the clamp 20 is not in use. A longitudinal slit 208 is provided along the bottom of the groove section 200 to allow the transmission link 164 to reciprocate therewithin. The solid section 194 of the spring housing 196 has two holes 204 through which threaded screws 206 can be extended to connect the spring housing 196 to two threaded openings (not shown) at the proximal end 198 of the handle piece 116.

The handle assembly 26 also includes a pivoting elongated handle piece 216 that has a longitudinal channel 218 provided on its inner surface 220. Two opposing walls 222 and 224 extend from the distal end of the handle piece 216 to define an internal space therebetween. Each wall 222 and 224 has a first opening 226 and 228, respectively, that are aligned with each other and through which a first pin 230 can be extended. Each wall 222 and 224 also has a second opening 232 that are aligned with each other and through which a second pin 236 can be extended. The internal space between the walls 222, 224 is adapted to receive the cylindrical tube of the tube housing 54, with the first pin 230 inserted through the first openings 226, 228, and an aligned opening 238 in the tube housing 54 to create a pivoting connection between the tube housing 54 and the handle piece 216. The internal space between the walls 222, 224 is also adapted to receive the distal end 240 of the transmission link 164, with the second pin 236 inserted through the second openings 232 and an aligned opening 242 in the distal end 240 to create a pivoting connection between the transmission link 164 and the handle piece 216. The longitudinal channel 218 is adapted to receive the transmission link 164 when the handle pieces 116 and 216 are gripped together (i.e., closed).

As shown in FIGS. 5 and 6, the proximal tube 42, the stop member 46 and the washers 50 are permanently secured inside the bore 110 of the tube housing 54 in the manner described above, with the stop member 46 abutting a shoulder 250 formed inside the bore 110. The cable 40 extends through the bores 38 of the beads 36, the bore 252 of the proximal tube 42, the stop member 46, and the longitudinal section 140 of the cable housing 128, and terminates at the bulbous end 142 that is retained inside the rounded section 138 of the cable housing 128.

The handle assembly 26 is normally biased to the open position that is shown in FIGS. 5 and 6. When a user grips the two handle pieces 116 and 216 together, the pivoting at the pins 230 and 236 will push the transmission link 164 in a proximal direction (see arrow A1), causing the hooked end 162 to overcome the normal bias of the spring 202 to pull the adjuster piece 130 and the cable housing 128 in the same proximal direction. As the cable housing 128 travels in the proximal direction, it will pull the bulbous end 142 of the cable 40 along with it, causing the cable 40 to be pulled in the proximal direction as well.

In this regard, the stop member 46, the proximal tube 42 and the beads 36 together provide the reaction force to tension the cable 40. The tension can be illustrated as follows: the locking hub 58 will abut the distal-most bead 36, and the other beads 36 will abut the proximal tube 42, which in turn abuts the stop member 46, which in turn abuts the shoulder 250 of the tube housing 54. Since the position of the tube housing 54 is fixed, and since the locking hub 58 is fixedly mounted to the stationary jaw housings (270 and 352 as described hereinbelow) of the gripping assemblies 30 and 30a, the beads 36, the proximal tube 42 and the stop member 46 are in compression. The cable 40 is then tensioned and is free to move, so that the jaws 260 and 262 of the gripping assembly 30 can be closed towards each other.

When the user's grip on the handle pieces 116, 216 is released, the spring 202 in the handle assembly 26 will bias the handle pieces 116, 216 open by pushing on the transmission link 164 in the distal direction (i.e., opposite to arrow A1). Simultaneously, the torsion spring 284 in the gripping assembly 30 (described in greater detail below, or springs 420 or 420A of FIG. 10B or 10C described below) will bias the jaws 260 and 262 open, and will pull the cable 40 in a distal direction (i.e., opposite to arrow A1).

The structure of the cable housing 128 and the adjuster piece 130 can be modified in accordance with another embodiment of the present invention. In this embodiment, the cable holder 128 and keyway 145 are omitted, and the end 142 of the cable 40 will be extended into the bore 150 of the adjuster piece 130 via the opening 168, and secured inside the bore 150 (e.g., by crimping).

The Gripping Assembly 30

Figure 10B:
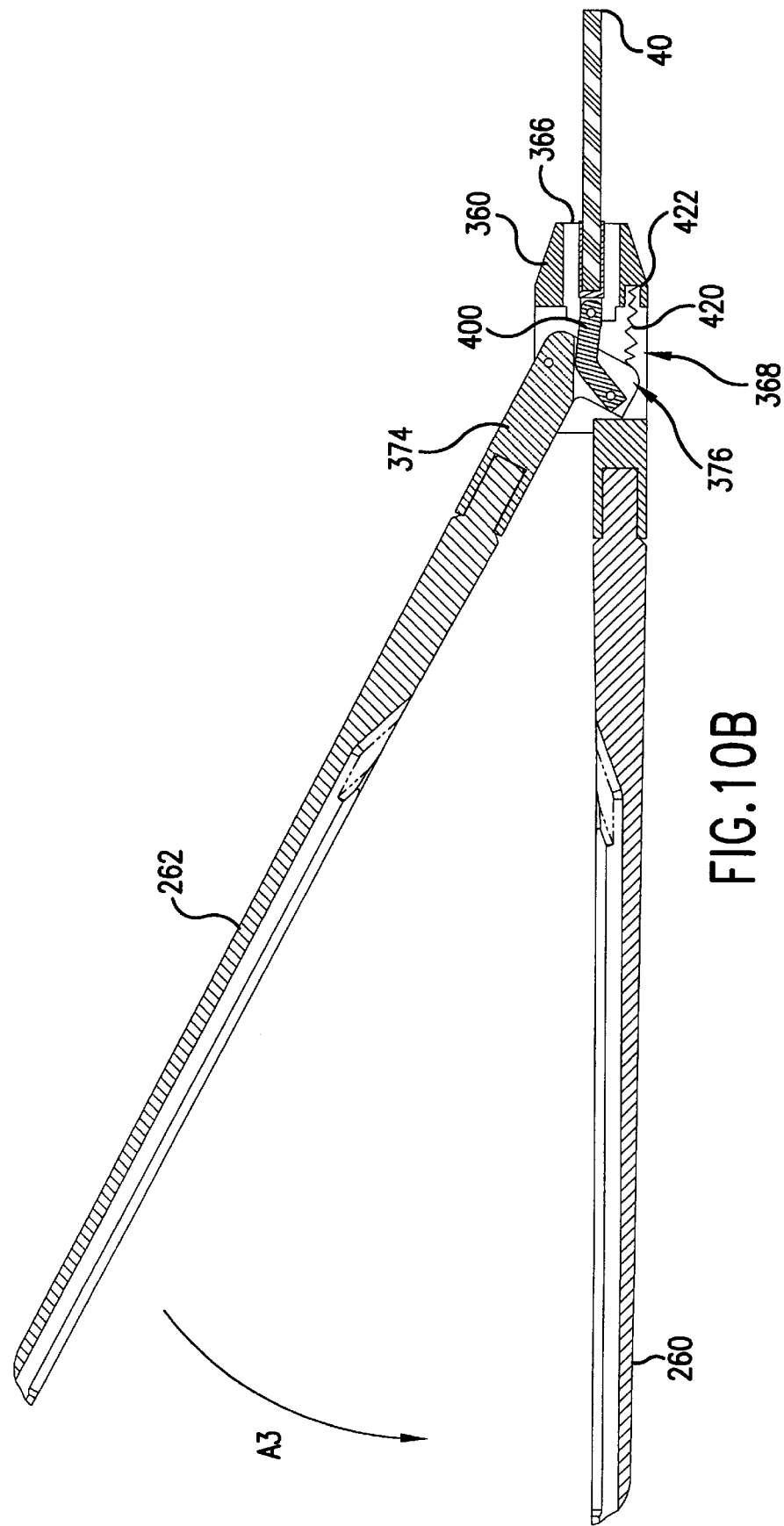
FIG. 10B is a cross-sectional view of the gripping assembly of FIG. 10A shown in the opened orientation.
Figure 10C:
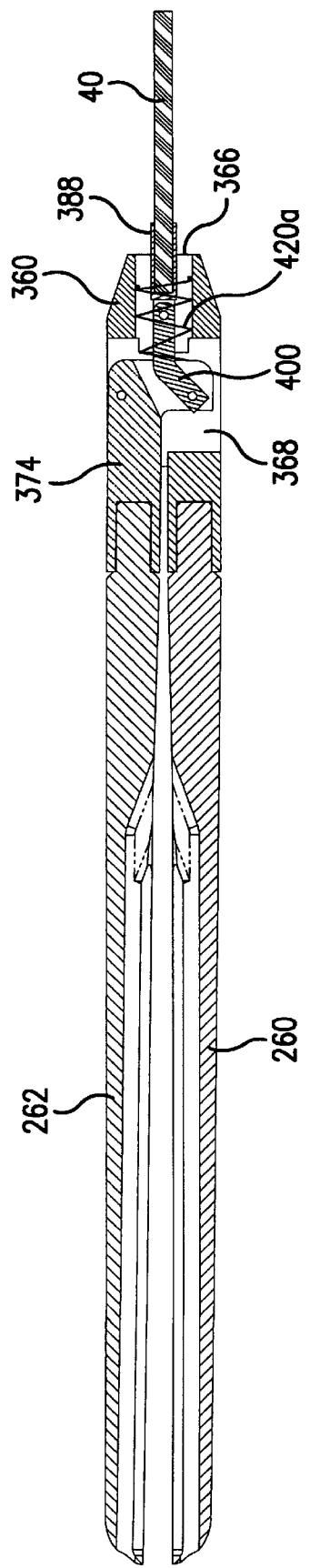
FIG. 10C is a cross-sectional view of the gripping assembly of FIG. 10A shown in the closed orientation.

One embodiment of the gripping assembly 30 is illustrated in connection with FIGS. 7–9. FIGS. 10A–10C illustrate another embodiment of the gripping assembly, labeled as 30a.

The gripping assembly 30 is used to grip a blood vessel to occlude the blood vessel during a surgical procedure. The gripping assembly 30 in FIG. 7A has a pair of gripping jaws 260 and 262 that can be pivoted to open and close with respect to each other. Each jaw 260 and 262 has an insert 264 provided thereon. These inserts 264 can be embodied in the form of any of the known inserts that are currently commercially available. The techniques and mechanisms for securing the inserts 264 to the jaws 260 and 262 are also well-known and will not be described herein.

Figure 7A:
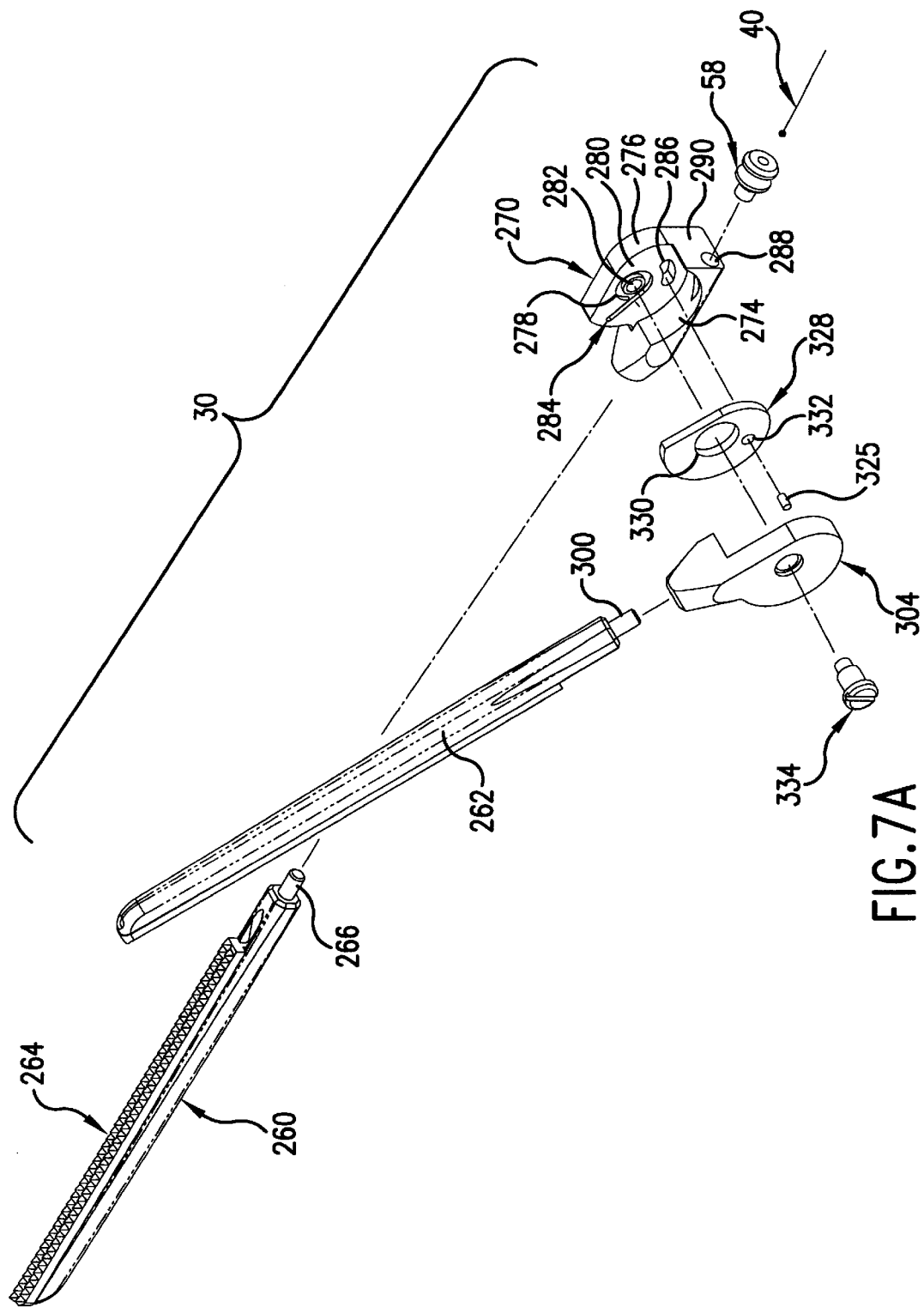
FIG. 7A is an exploded perspective view of one embodiment of the gripping assembly of the clamp of FIG. 1.
Figure 7B:
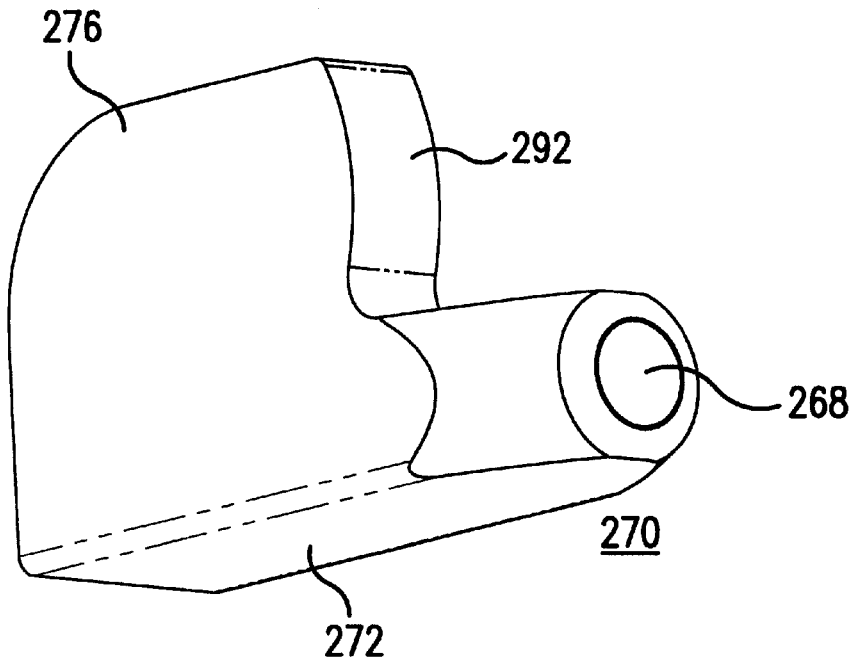
FIG. 7B is a side perspective view of a stationary jaw base of the gripping assembly of FIG. 7A.
Figure 8:
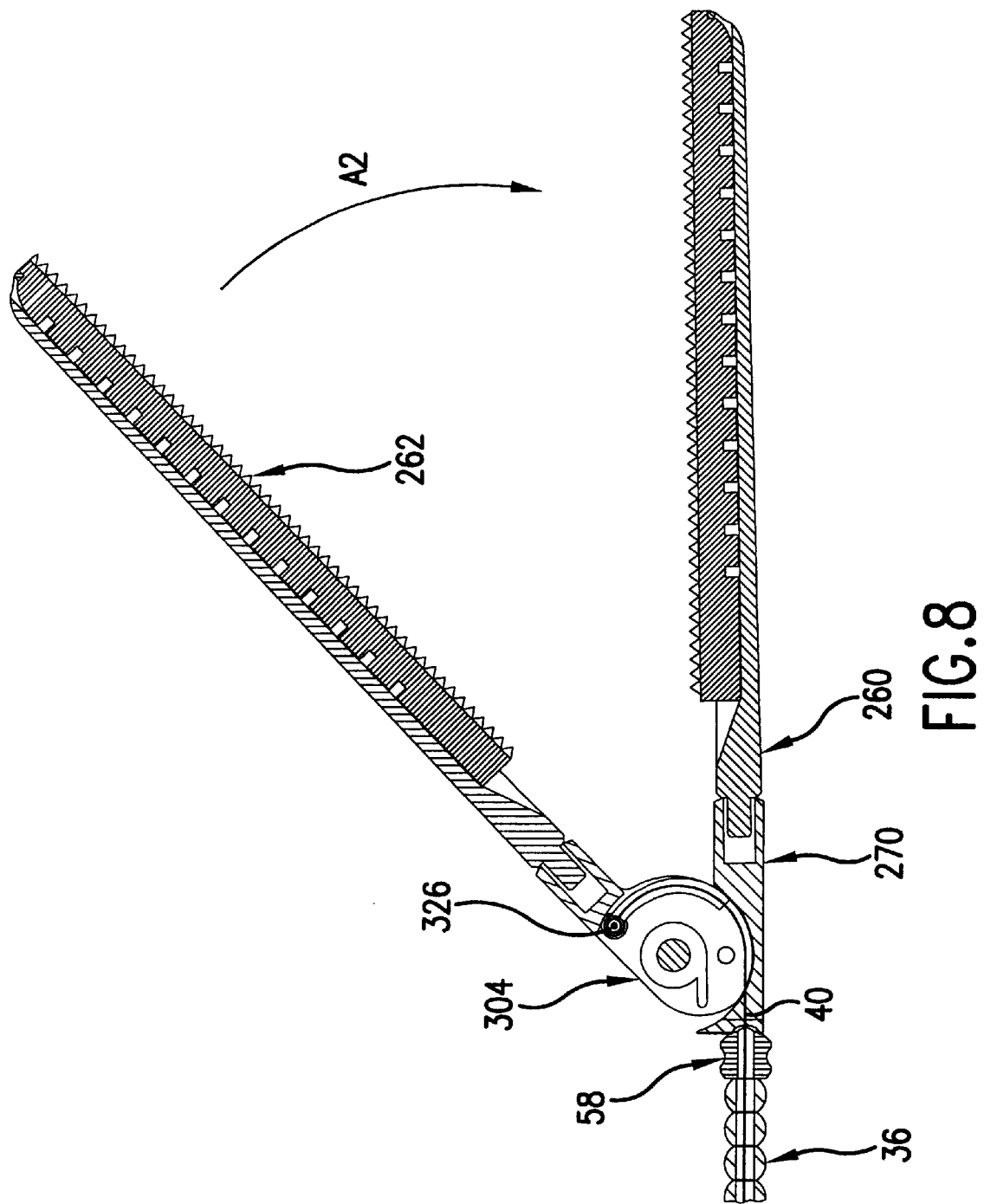
FIG. 8 is a cross-sectional view of the gripping assembly of FIG. 7A without the telescoping tubes deployed over the shaft.

Referring to FIGS. 7A and 7B, the proximal end 266 of the first jaw 260 is secured inside a bore 268 of a stationary jaw base 270. The jaw base 270 has a base section 272 that has a concave upper surface 274, and includes the bore 268 at a distal portion thereof. A vertical wall 276 extends from the base section 272 and has a recess 278 in its inner surface 280 that is configured like the numeral "6" with a round hollow shaft 282 positioned at about the center of the base of the "6". The hollow shaft 282 has internal threads. A torsion spring 284 is retained inside the recess 278 about the shaft 282, with one leg of the torsion spring 284 retained in the straight part of the "6" of the recess 278. A curved recess 286 is provided in the vertical wall 276 and is adapted to receive a dowel pin 325. The vertical wall 276 has a distal surface 292 with a convex curvature. An opening 288 is provided in the proximal end 290 of the base section 272 and communicates with the location of the concave surface 274. The shaft 65 of the locking hub 58 is fitted into the opening 288 and permanently retained (e.g., by welding or bonding) therein.

Figure 7C:
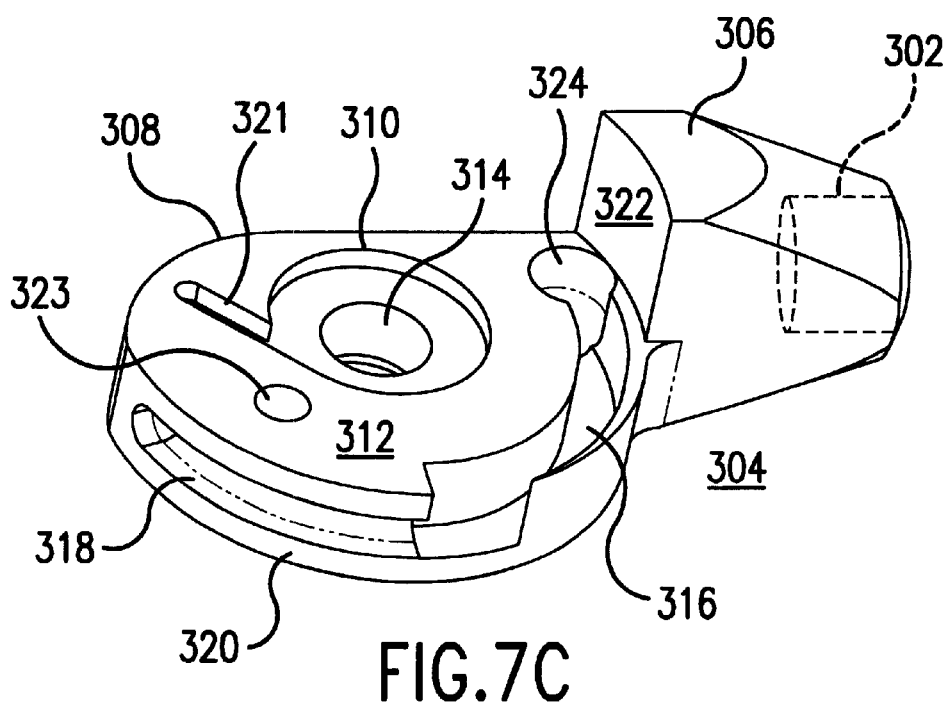
FIG. 7C is a side perspective view of a pivoting jaw base of the gripping assembly of FIG. 7A.

Referring to FIGS. 7A and 7C, the proximal end 300 of the second jaw 262 is secured inside a bore 302 of a pivoting jaw base 304. The jaw base 304 has a connecting head 306 that houses the bore 302, and a vertical wall piece 308. The vertical wall piece 308 has a recess 310 in its inner surface 312 that is configured like the numeral "6" with a round hole 314 positioned at about the center of the base of the "6". The recess 310 is configured to be aligned with the recess 278 of the jaw base 270, so that part of the torsion spring 284 can also be retained inside the recess 310. However, the numeral "6" configuration for the recess 310 is reversed from the numeral "6" configuration for the recess 278 of the jaw base 270, so that an opposing leg of the torsion spring 284 is retained in the straight part (e.g., 321) of the "6" of the recess 310. With each opposing leg of the torsion spring 284 retained in separate straight parts of the two different recesses 278 and 310, the torsion spring 284 will be securely retained between the two jaw bases 270 and 304.

In addition, a first curved slot 316 is provided along the lower periphery of the vertical wall piece 308 and extends inwardly from the inner surface 312. The first slot 316 extends from a bulbous or enlarged region 324 adjacent the connecting head 306 and then travels along the lower periphery of the vertical wall piece 308 to be in communication with a second curved slot 318. The second curved slot 318 also extends along the lower periphery of the vertical wall piece 308, but extends inwardly not from the inner surface 312, but from the bottom surface 320 of the vertical wall piece 308. As shown in FIG. 8, a bulbous distal end 326 of the cable 40 is retained in the bulbous region 324 of the first slot 316. The cable 40 is then retained inside and extends along the first slot 316 and the second slot 318, exiting the second slot 318 at the bottom surface 320 to extend through the opening 288 of the jaw base 270 into the locking hub 58 and then through the bores 38 of the beads 36. The proximal wall 322 of the connecting head 306 has a concave curvature that is configured to complement the convex curvature of the distal surface 292 of the jaw base 270. In addition, a hole 323 is provided on the inner surface 312 of the jaw base 304 for receiving a dowel pin 325. The hole 323 and dowel pin 325 are aligned with the curved recess 286.

A shim 328 is provided between the inner surfaces 280 and 312 of the jaw bases 270 and 304, respectively. The shim 328 has a central opening 330 that is aligned with the recesses 278 and 310 of the jaw bases 270 and 304, respectively. The shim 328 also has a through-hole 332 that is aligned with the hole 323 and the curved recess 286, and through which the dowel pin 325 extends. The shim 328 facilitates smooth rotation of the pivoting jaw base 304 with respect to the jaw base 270. This smooth rotation is accomplished by good surface finish and low coefficient of friction between the shim 328 and the surface 312 of the pivoting jaw base 304.

The gripping assembly 30 is assembled by positioning the shim 328 between the jaw bases 270 and 304, and extending a shoulder screw 334 through the round hole 314 and the opening 330 in the shim 328, with the shoulder screw 334 threadably coupled to the internal threads inside the hollow interior of the shaft 282. As a result, the jaw base 304 pivots with respect to the jaw base 270 about the pivot point defined by the screw 334. More specifically, the jaw base 270 is stationary, and the jaw base 304 pivots about the jaw base 270 with the surface of the proximal wall 322 on the jaw base 304 sliding up and down with respect to the surface 292 on the jaw base 270. In addition, the dowel pin 325 extends into the curved recess 286 and reciprocates in the curved recess 286. The opposing ends of the curved recess 286 define stop surfaces to limit the extent of the rotation of the pivoting jaw base 304 in either direction.

The torsion spring 284 provides a torque which biases the jaws 260 and 262 open. Therefore, when the handle assembly 26 is opened, the tension in the cable 40 is relieved and the torsion spring 284 will bias the pivoting jaw base 304 to open with respect to the stationary jaw base 270.

The operation of the clamp 20 can be understood by referring to FIGS. 1, 2, 5, 6, 8 and 9. When not in use, the handle pieces 116 and 216 are normally spaced apart from each other in an open position, and the jaws 260 and 262 are also normally spaced apart from each other in an open position. At this time, the telescoping tubes 32 can be deployed to cover the shaft 22 (see FIGS. 1, 5 and 9), or the telescoping tubes 32 can be nested and stored inside the tube housing 54 (see FIGS. 2, 6 and 8). When the telescoping tubes 32 are nested and stored inside the tube housing 54 (see FIGS. 2, 6 and 8), the inner lock housing 72 and the outer lock housing 74 are positioned at the proximal end 24 of the shaft 22 adjacent the tube housing 54. When the telescoping tubes 32 are deployed to cover the shaft 22 (see FIGS. 1, 5 and 9), the inner lock housing 72 and the outer lock housing 74 are secured to the locking hub 58 at the distal end 28 of the shaft 22 adjacent the jaw base 270 in the manner described above.

When the clamp 20 is used to grip a blood vessel, the surgeon introduces the jaws 260, 262 through a trocar or a surgical site using known surgical techniques, and grips the handle pieces 116 and 216 to bring them together. As the handle pieces 116 and 216 are brought together, the cable 40 is pulled in the proximal direction (see arrow A1 in FIG. 6) in the manner described hereinabove. As the cable 40 is pulled in the proximal direction, the tension in the cable 40 produces a torque in the pivoting jaw base 304 in the direction of arrow A2 in FIG. 8. This torque increases to the point that the torque from the torsion spring 284 (which biases the jaw 262 open) is overcome and the jaw 262 pivots or closes towards the other jaw 260 in the direction of arrow A2 to grip the blood vessel.

Figure 13:
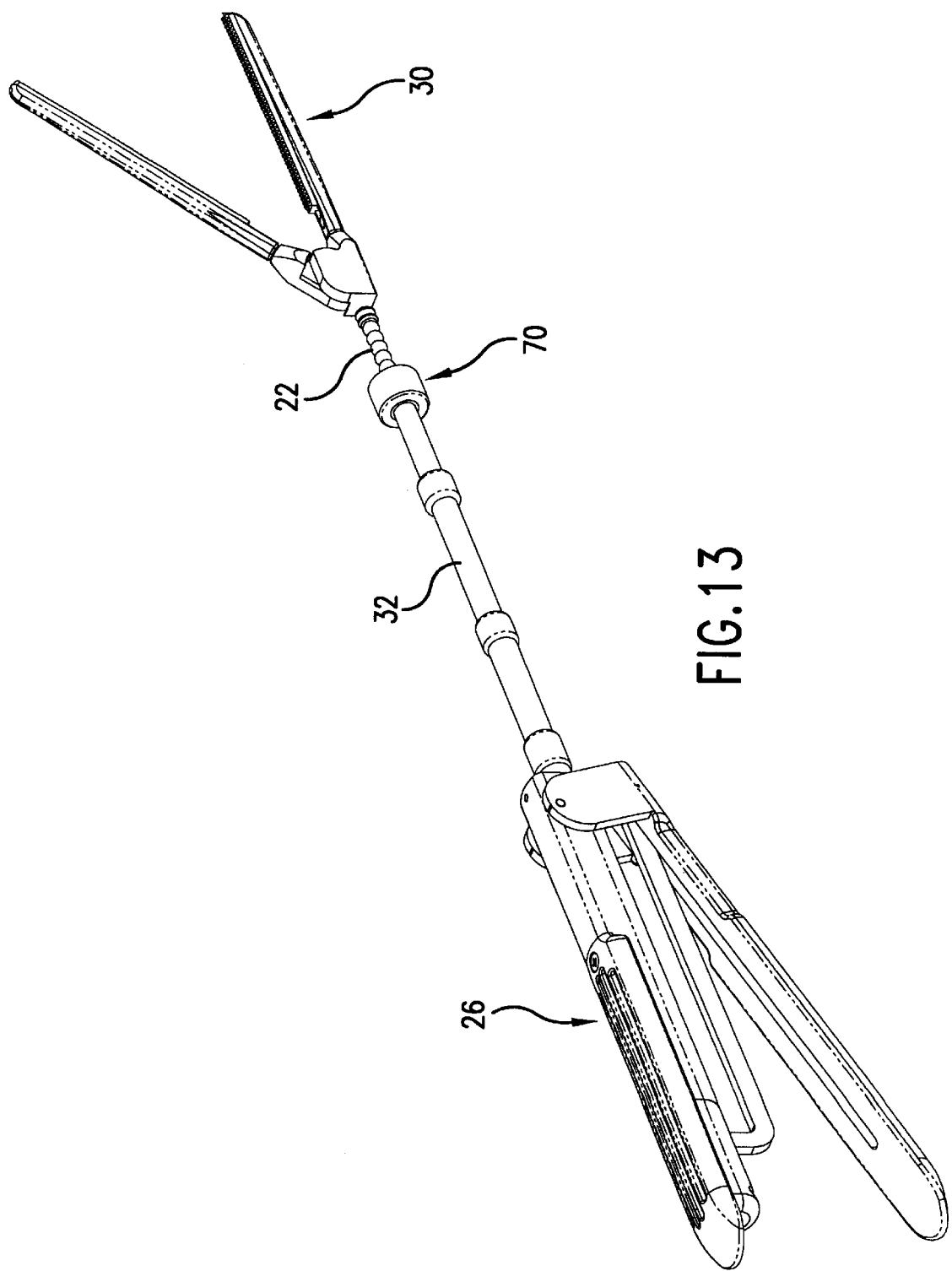
FIG. 13 is a perspective view of the clamp of FIG. 1 with the shaft partially covered by telescoping tubes.

When the jaws 260, 262 have gripped a blood vessel, the surgeon can retract the telescoping tubes 32. The surgeon can completely retract the telescoping tubes 32 to have all the telescoping tubes 32 nested and stored inside the tube housing 54 (see FIGS. 2, 6 and 8), thereby exposing the entire shaft 22. Alternatively, the surgeon can retract some, but not all, of the telescoping tubes 32 (see FIG. 13) so that only a portion (but not the entire length of) the shaft 22 is exposed. The exposed portions of the shaft 22 will then be bendable by the surgeon in any direction desired by the surgeon, so that the handle assembly 26 can be moved away from the surgical site and not impede the surgeon's access to the surgical site.

When the surgeon releases the grip on the handle pieces 116 and 216, the spring 202 biases the handle pieces 116 and 216 apart from each other by pushing on the transmission link 164 in the distal direction (i.e., opposite to arrow A1). This relieves the tension in the cable 40, so that the torsion spring 284 can simultaneously bias the jaws 260 and 262 open, thereby pulling the cable 40 in the distal direction.

The Gripping Assembly 30a

Another embodiment of the gripping assembly 30a is illustrated in connection with FIGS. 10A–10C. The gripping assembly 30a in FIGS. 10A–10C also has a pair of gripping jaws 260 and 262 that can be pivoted to open and close. Each jaw 260 and 262 has an insert 264 provided thereon. These inserts 264 and the jaws 260 and 262 can be the same as those described above in connection with FIG. 7A.

The proximal end 266 of the first jaw 260 is secured inside a bore 350 of a stationary jaw base 352. The jaw base 352 has a distal tubular section 354 that defines the bore 350, a holder section that has a pair of opposing vertical walls 356 and 358, and a proximal tubular section 360 that is attached to the locking hub 58 (not shown in FIG. 10A). The opposing vertical walls 356 and 358 define a space 368 therebetween, and each vertical wall 356 and 358 has an aligned opening 362 and 364, respectively. The proximal tubular section 360 has a bore 366 through which a portion of the cable 40 can extend.

The proximal end 300 of the second jaw 262 is secured inside a bore 370 of a pivoting jaw base 372. The jaw base 372 has an L-shaped configuration, with a longitudinal portion 374 that defines the bore 370, and a transverse portion 376 that has a first hole 378. The transverse portion 376 is comprised of two parallel walls that define a space therebetween, and with aligned second holes 380 provided in each parallel wall.

A cable fitting 388 has a proximal bore into which the distal-most end of the cable 40 is fitted and secured (see FIGS. 10B and 10C). The distal part of the cable fitting 388 has two opposing walls 390 and 392 that define a space therebetween.

A jaw transmission link 400 is provided in an angled configuration having a distal portion 402 that is angled with respect to a proximal portion 404. The distal portion 402 has an opening 406, and the proximal portion 404 has its own opening 408. The distal portion 402 is fitted between the two parallel walls of the transverse portion 376, with the opening 406 aligned with the second holes 380.

The cable fitting 388 carries the distal end of the cable 40 and extends through the bore 366 of the jaw base 352 and into the space 368. The proximal portion 404 of the transmission link 400 is received in the space between the two opposing walls 390 and 392 of the cable fitting 388 with the opening 408 of the proximal portion 404 aligned with an opening 410 on each of the walls 390 and 392. A dowel pin 412 extends through the opening 408 of the proximal portion 404 and the openings 410 on each of the walls 390 and 392 to create a pivoting connection between the cable fitting 388 and the proximal portion 404. In addition, the opening 406 of the distal portion 402 of the transmission link 400 is aligned with the second hole 380 of the jaw base 372, so that another dowel pin 414 can extend through the opening 406 and the second hole 380 to create a pivoting connection between the jaw base 372 and the distal portion 402. Yet another dowel pin 416 can be extended through the aligned openings 362 and 364 on the walls 356 and 358, respectively, of the jaw base 352 and the first hole 378 on the jaw base 372, to create a pivoting connecting between the jaw bases 352 and 372.

A spring 420 is provided inside the jaw base 352 to bias the pivoting jaw base 372 with respect to the stationary jaw base 352. In one embodiment shown in FIG. 10B, the spring 420 can be retained inside the space 368, and have a first end attached to the transverse portion 376 of the jaw base 372 and a second end secured inside a bore 422 in the proximal tubular section 360. In another embodiment shown in FIG. 10C, the spring 420a can be wrapped around the transmission link 400 and the cable fitting 388. As a further alternative, a leaf spring or torsion spring can also be provided to perform the same function.

The operation of the gripping assembly 30a will be described as follows. When the clamp 20 is used to grip a blood vessel, the surgeon grips the handle pieces 116 and 216 to bring them together. As the handle pieces 116 and 216 are brought together, the cable 40 is pulled in the proximal direction (see arrow A1 in FIG. 6) in the manner described hereinabove. As the cable 40 is pulled in the proximal direction, the distal end of the cable 40 pulls the cable fitting 388 in the proximal direction. The cable fitting 388 rotates the transverse portion 376 of the jaw base 372 in the direction of arrow A3 shown in FIG. 10B about the axis defined by the dowel pin 416. This causes the pivoting jaw base 372 to pivot towards the stationary jaw base 352 to grip the blood vessel.

As with the other embodiments, when the jaws 260, 262 have gripped a blood vessel, the surgeon can retract the telescoping tubes 32 completely to nest and store all the telescoping tubes 32 inside the tube housing 54, or the surgeon can retract some, but not all, of the telescoping tubes 32 so that only a portion (but not the entire length of) the shaft 22 is exposed. The exposed portions of the shaft 22 will then be bendable by the surgeon in any direction desired by the surgeon, so that the handle assembly 26 can be moved away from the surgical site and not impede the surgeon's access to the surgical site.

When the surgeon releases the grip on the handle pieces 116 and 216, the spring 202 biases the handle pieces 116 and 216 apart from each other in the manner described above, and the spring 420 or 420a biases the jaw base 372 away from the jaw base 352.

Thus, the present invention provides a clamping device (the clamp assembly 20) that can effectively clamp a blood vessel at a surgical site, while not interfering with the surgeon's access to the surgical site. The shaft assembly that includes a flexible shaft and nested telescoping tubes 32 allows the shaft assembly to be both completely rigid and completely flexible. The rigid shaft that is formed when the telescoping tubes 32 are fully deployed is capable of withstanding axial loads, side loads, moments and torques applied to the jaws 260, 262. As a result, the surgeon can use the jaws 260, 262 to poke and prod around the surgical site.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A clamp, comprising:
   a handle assembly;
   a gripping assembly having a pair of jaws that can be opened and closed to grip an element; and
   a shaft assembly having:
      a flexible shaft having a proximal end that is coupled to the handle assembly and a distal end that is coupled to the gripping assembly, the flexible shaft defining a bore;
      a cable which extends through the bore of the flexible shaft, the cable having a proximal end that is operatively coupled to the handle assembly and a distal end that is operatively coupled to the gripping assembly; and
      a plurality of rigid telescoping tubes that can be oriented in a first position where the telescoping tubes are nested within each other, and in a second position where the telescoping tubes are fully deployed to completely cover the flexible shaft.

2. The clamp of claim 1, wherein the plurality of telescoping tubes has a distal telescoping tube that is locked to the gripping assembly when the telescoping tubes are oriented in the second position.

3. The clamp of claim 1, wherein the plurality of telescoping tubes has a proximal telescoping tube that is secured to the handle assembly.

4. The clamp of claim 1, wherein the plurality of telescoping tubes has a proximal telescoping tube, a distal telescoping tube, and at least one intermediate telescoping tube between the proximal telescoping tube and the distal telescoping tube, and wherein the size of each of the plurality of telescoping tubes progressively decreases from the proximal telescoping tube to the distal telescoping tube.

5. The clamp of claim 1, wherein the shaft is completely flexible when the plurality of telescoping tubes is in the first position.

6. The clamp of claim 5, wherein the flexible shaft is capable of withstanding axial loads when the plurality of telescoping tubes is in the first position.

7. The clamp of claim 1, wherein the flexible shaft comprises a plurality of beads, each having a bore through which the cable extends.

8. The clamp of claim 1, further including a locking hub positioned at the distal end of the shaft, and a locking mechanism positioned on the distal-most telescoping tube, with the locking mechanism removably engaging the locking hub to secure the plurality of telescoping tubes in the second position.

9. The clamp of claim 1, wherein the handle assembly includes:
   a proximal tube having a distal end coupled to the proximal end of the flexible shaft, and with the plurality of telescoping tubes slidable over the proximal tube.

10. The clamp of claim 1, wherein the handle assembly includes:
   a calibration assembly coupled to the proximal end of the cable for adjusting the tension of the cable.

11. The clamp of claim 10, wherein the calibration assembly includes:
   a cable holder that retains the proximal end of the cable; and
   an adjuster piece having a coupling mechanism that couples the cable holder.

12. The clamp of claim 10, wherein the calibration assembly includes:
   a stop member positioned in the handle assembly;
   a proximal tube retained in the handle assembly and having a proximal end that is threadably connected to the stop member; and
   a plurality of washers positioned at the threaded connection between the proximal tube and the stop member.

13. The clamp of claim 1, wherein the handle assembly includes:
   a first handle piece;
   a second handle piece pivotable with respect to the first handle piece;
   a transmission link coupled to the second handle piece and the cable; and
   a resilient element biasing the transmission link in a distal direction.

14. The clamp of claim 1, wherein the plurality of telescoping tubes are non-rotational.

15. The clamp of claim 1, wherein the jaws are non-rotational and are capable of supporting axial loads, side loads, moments, and torques.

16. The clamp of claim 1, wherein the plurality of telescoping tubes are nested inside the handle assembly in the first position.

17. A clamp, comprising:

a handle assembly;

a gripping assembly having a pair of jaws that can be opened and closed to grip an element; and a shaft assembly having:
 a flexible shaft having a proximal end that is coupled to the handle assembly and a distal end that is coupled to the gripping assembly, the flexible shaft defining a bore;
 a cable which extends through the bore of the flexible shaft, the cable having a proximal end that is operatively coupled to the handle assembly and a distal end that is operatively coupled to the gripping assembly; and
 a retractable generally rigid covering that can be oriented in a first position where the covering exposes a portion of the flexible shaft, and in a second position where the covering completely covers the flexible shaft.

18. The clamp of claim 17, wherein the covering has a distal end that is locked to the gripping assembly when the covering is oriented in the second position.

19. The clamp of claim 18, wherein the covering has a proximal end that is secured inside the handle assembly.

20. The clamp of claim 19, wherein the covering progressively decreases in size from its proximal end to its distal end.

21. The clamp of claim 17, wherein the shaft is completely flexible when the covering is in the first position.

22. The clamp of claim 17, wherein the flexible shaft comprises a plurality of beads, each having a bore through which the cable extends.

23. The clamp of claim 17, wherein the rigid covering is non-rotational.

24. A surgical method, comprising:

a. providing a clamp, comprising:
 a handle assembly;
 a gripping assembly having a pair of jaws that can be opened and closed to grip an element; and
 a shaft assembly having a flexible shaft having a proximal end that is coupled to the handle assembly and a distal end that is coupled to the gripping assembly, and a retractable rigid covering that completely covers the flexible shaft so that a region of the flexible shaft is generally rigid;

b. introducing the jaws through a surgical site or a trocar;

c. closing the jaws to grip a blood vessel;

d. withdrawing the covering from the flexible shaft so that a portion of the region of the flexible shaft is completely flexible; and e. moving the handle assembly away from the surgical site.

25. The method of claim 24, wherein step (d) includes retaining the withdrawn covering inside the handle assembly.

26. A clamp comprising:

a handle assembly;

a gripping assembly having a pair of jaws that can be opened and closed to grip an element; and a shaft assembly having:
 a flexible elongate member having a proximal end that is operatively coupled to the handle assembly and a distal end that is operatively coupled to the gripping assembly; and
 a movable covering coaxial to the elongate member that can be placed in a first position where the covering exposes a portion of the flexible shaft, and in a second position where the covering covers a substantial portion of the flexible shaft.

* * * * *